United States Patent
Subramaniam et al.

(10) Patent No.: US 11,344,702 B2
(45) Date of Patent: May 31, 2022

(54) STEERABLE SHEATH

(71) Applicant: Vizaramed, Inc., Fremont, CA (US)

(72) Inventors: Raj Subramaniam, Fremont, CA (US); Zaya Tun, Livermore, CA (US); Robert Quintos, Newark, CA (US)

(73) Assignee: Vizaramed, Inc., Fremont, CA (US)

( * ) Notice: Subject to any disclaimer, the term of this patent is extended or adjusted under 35 U.S.C. 154(b) by 126 days.

(21) Appl. No.: 16/944,997

(22) Filed: Jul. 31, 2020

(65) Prior Publication Data

US 2021/0031006 A1 Feb. 4, 2021

Related U.S. Application Data

(60) Provisional application No. 62/882,050, filed on Aug. 2, 2019.

(51) Int. Cl.
*A61M 25/01* (2006.01)
*A61M 25/00* (2006.01)
*A61M 29/00* (2006.01)

(52) U.S. Cl.
CPC .... *A61M 25/0147* (2013.01); *A61M 25/0041* (2013.01); *A61M 25/0054* (2013.01); *A61M 25/0136* (2013.01); *A61M 29/00* (2013.01); *A61M 2025/0062* (2013.01); *A61M 2025/015* (2013.01)

(58) Field of Classification Search
CPC .......... A61M 25/0147; A61M 25/0041; A61M 25/0054; A61M 2025/0062; A61M 2025/015; A61M 29/00
See application file for complete search history.

(56) References Cited

U.S. PATENT DOCUMENTS

| | | | |
|---|---|---|---|
| 6,468,203 B2 | 10/2002 | Belson | |
| 10,278,852 B2 | 5/2019 | Griffin | |
| 2019/0192820 A1* | 6/2019 | Olson | A61M 25/0136 |

FOREIGN PATENT DOCUMENTS

| | | |
|---|---|---|
| WO | 2018017717 | 1/2018 |
| WO | WO-2018017717 A1 | 1/2018 |
| WO | 2019038337 | 2/2019 |
| WO | WO-2019038337 A1 | 2/2019 |
| WO | WO-2021026019 A1 | 2/2021 |

OTHER PUBLICATIONS

"International Application Serial No. PCT US2020 044578, International Search Report dated Oct. 22, 2020", 2 pages.
"International Application Serial No. PCT US2020 044578, Written Opinion dated Oct. 22, 2020", 6 pages.
"International Application Serial No. PCT/US2020/044578, International Search Report dated Oct. 22, 2020", 2 pgs.
"International Application Serial No. PCT/US2020/044578, Written Opinion dated Oct. 22, 2020", 6 pgs.

* cited by examiner

*Primary Examiner* — Nathan R Price
*Assistant Examiner* — Melissa A Snyder
(74) *Attorney, Agent, or Firm* — Schwegman Lundberg & Woessner, P.A.

(57) ABSTRACT

A steerable sheath includes an elongate shaft, a handle, an actuator element on the handle, and a plurality of control wires operably coupled to the elongate shaft and the actuator element. Actuation of the actuator element adjusts a shape of a proximal curve and a distal curve on the elongate shaft.

29 Claims, 15 Drawing Sheets

STEERABLE SHEATH

CLAIM OF PRIORITY

The present application is a non-provisional of, and claims the benefit of U.S. Provisional Patent Application No. 62/882,050 filed on Aug. 2, 2019; the entire contents of which are incorporated herein by reference.

BACKGROUND

Many minimally invasive catheter procedures use a guidewire to serve as a rail over which a sheath may be advanced toward a target treatment area. The sheath facilitates delivery of a therapeutic or diagnostic device to the target treatment area. Some sheaths may be pre-curved to match a patient's anatomy to help direct the catheter to the target area.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Many minimally invasive catheter procedures use a guidewire to serve as a rail over which a sheath may be advanced toward a target treatment area. The sheath facilitates delivery of a therapeutic or diagnostic device to the target treatment area. Or the sheath may be used to deliver a therapeutic or diagnostic agent to the target treatment area. Some sheaths may be pre-curved to match a patient's anatomy to help direct the therapeutic or diagnostic device to the target area. Many shapes may be required to match varying patient anatomies and therefore large inventories of sheaths may be needed. Furthermore, it may be challenging to provide pre-curved sheaths that match all patient anatomies. Therefore, it would be desirable to provide a sheath that can accommodate a more diverse set of anatomies.

Examples of steerable sheaths are disclosed herein and are generally related to a long tubular conduit for delivering a diagnostic or therapeutic medical device, including implants, to a target treatment site. Also, steerable sheaths disclosed herein may be used to assist with delivering certain pharmacological agents such as in targeted therapies, or a diagnostic agent such as contrast medium. The sheath optionally may have a hemostasis valve that can be completely closed to prevent the loss of any blood when inserted into the heart of the patient through an artery or a vein, or any other part of the vasculature that results in blood leakage from the sheath. The sheath may have a handle with an optional flexible side-port attached to an optional three-way stopcock for aspiration and infusion of fluids. The handle houses mechanisms that are connected to pull wires (also referred to herein as control wires) that terminate in the pull wire ring(s) at the distal section of the sheath. When these mechanisms in the handle are actuated, the distal section(s) of the tubular portion of the sheath will deflect or bend in a predictable and controlled manner.

Figure 1:
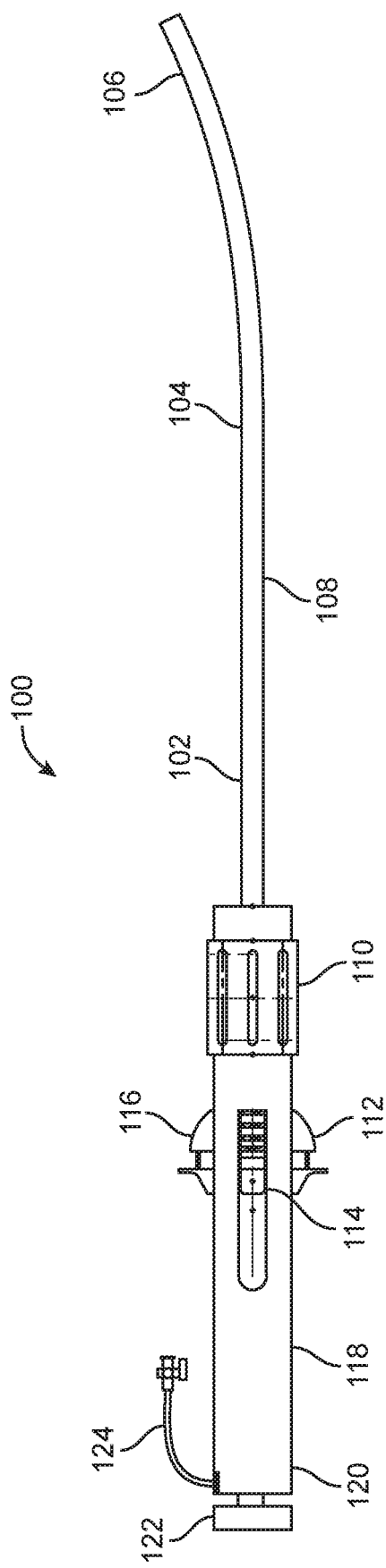
FIG. 1 illustrates an example of steerable sheath.

FIG. 1 shows an example of a steerable sheath 100. The sheath 100 includes an elongate shaft 108 having a proximal portion 102, a distal portion 106, and a middle or intermediate portion 104 between the proximal and distal portions 102, 106.

There may be a transitional segment between distal portion 106 and intermediate portion 104 that has a different durometer than either distal or intermediate portions 106, 104. For example, the transitional segment may have a durometer of about 55 Shore D and this helps prevent kinking as well as allows smoother tracking. The transitional segment may therefore be stiffer than the intermediate portion 104 and less stiff than the proximal portion 102.

A lumen extends along the length of the elongate shaft and is sized and shaped to slidably receive a therapeutic or diagnostic device. Thus, once placed, the sheath provides a direct path to the target treatment area and protects the therapeutic or diagnostic device as it is advanced toward to treatment area as well as preventing the therapeutic or diagnostic device from causing trauma to the tissue as it is delivered.

The proximal portion 102 of the elongate shaft 108 is coupled to the distal end of a handle 118. The handle 118 includes an actuator 110 or actuators that may be operably coupled with the intermediate portion 104 of the elongate shaft 108 such that actuation of the actuator 110 will form a proximal curve in the intermediate portion 104. Here, the actuator(s) may be any mechanism for controlling the proximal curve or proximal curves, but here the actuator is a rotatable wheel. The handle also may include one or more additional actuators 112, 114, 116 that are operably coupled to the distal portion 106 of the elongate shaft 108. Actuation of one or more of actuators 112, 114, 116 will form a distal curve along the distal portion 106 of the elongate shaft. Here, only three additional actuators 112, 114, 116 are shown but a forth actuator is also included on the handle but is not visible in this view. The actuators may be any mechanism for controlling the distal curve, but here the actuators 112, 114, 116 are sliders. The handle includes a body that is sized and shaped for comfortable handling and manipulation by an operator. The proximal end 120 of the handle 118 may include a hemostasis valve such as a duckbill valve or a Tuohy-Borst valve that prevents blood or other fluid from exiting the lumen in the sheath and helps hold guidewires or other shafts which may be inserted into the catheter lumen. The diagnostic or therapeutic device may be inserted into the lumen at the proximal end of the handle and advanced through the sheath lumen until it exits the distal end of the sheath which is positioned adjacent the target treatment area.

Optionally, a side port 124 maybe coupled to the proximal end 120 of the handle 118 and a one-way or multi-way stopcock may be used to open and close the fluid pathway of the side port which is fluidly coupled to the lumen of the sheath. Thus, the side port may be used to introduce a fluid into the lumen or to remove fluid such as blood from the lumen. Fluids such as saline may be used to flush the lumen to remove air from the lumen prior to use, or a therapeutic agent may be introduced into the lumen via the side port and delivered to the treatment region. Additional details about the actuators and how they form the proximal and distal curves are disclosed below.

Figure 2A:
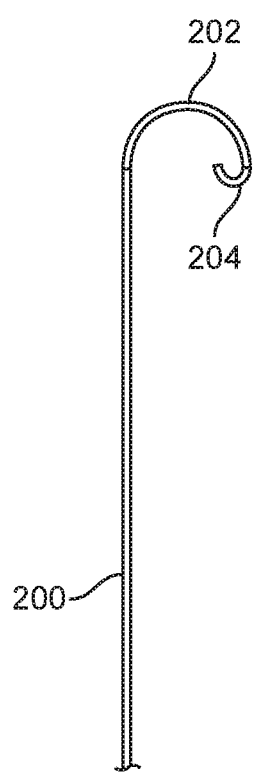
FIGS. 2A-2E show examples of curves in a steerable sheath.

FIGS. 2A-2E show examples of curves that may be formed in a steerable sheath 200 such as in FIG. 1, or any steerable sheath disclosed herein. In FIG. 2A, the proximal curve 202 is formed in a first plane and the distal curve 204 is formed in the same first plane. The distal curve has a smaller radius of curvature than the proximal curve.

Figure 2B:
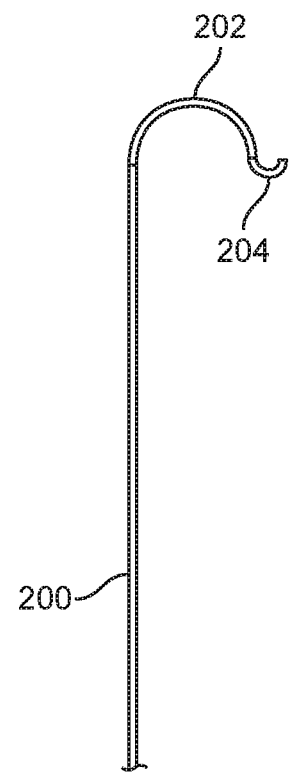

In FIG. 2B the proximal curve 202 is formed in a first plane and the distal curve 204 is also formed in the same first plane, but this time the distal curve is in the opposite direction as the distal curve in FIG. 2A. The distal curve 204 in FIG. 2B has a smaller radius of curvature than the proximal curve 202.

Figure 2C:
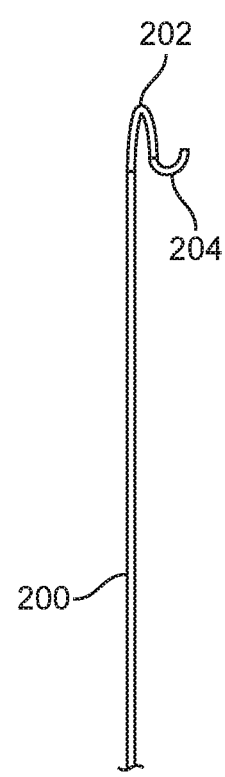

In FIG. 2C the proximal curve 202 is formed in a first plane (the figure is rotated relative to FIGS. 2A-2B for ease in viewing the planes) and the distal curve 204 is formed in a second plane that is transverse to the first plane and the second plane may be orthogonal to the first plane. Thus, the distal curve extends out of the plane in which the proximal curve lies.

Figure 2D:
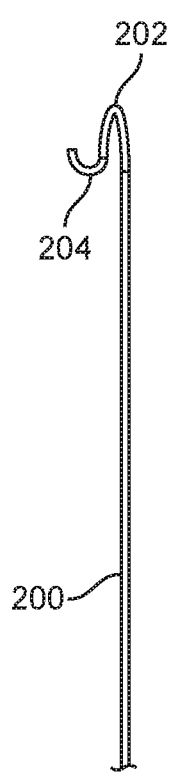

In FIG. 2D (similar rotation as in FIG. 2C) the proximal curve 202 is formed in a first plane and the distal curve 204 is formed in a second plane that is transverse to the first plane and the second plane may be orthogonal to the first plane. This is similar to the example in FIG. 2C except that the distal curve is in the opposite direction as the distal curve in FIG. 2C. The distal curve in FIG. 2D has a smaller radius of curvature than the proximal curve.

FIGS. 2A-2D show the proximal curve in a single direction. However, the proximal curve may be also be formed in a second direction opposite the first direction thereby forming a bidirectional proximal curve. Moreover, any combination of proximal and distal curves may be formed. For example, the proximal curve may be formed in a first direction or a second direction opposite the first direction, and the proximal curve in the first or second directions may lie in a first plane. The curve forming mechanism for the proximal curve (such as those described herein) may also be duplicated thereby allowing the proximal curve to be formed in a third direction and a fourth direction opposite the third direction thereby allowing formation of quad-directional curve (also referred to as a multi-directional curve) either in the first plane or in a second plane orthogonal or transverse to the first plane. The proximal curve in any of these configurations maybe combined with a distal curve that can curve in a first direction or a second direction opposite the first direction, and the distal curve can lie in the first plane, or in a second plane that is transverse or orthogonal to the first plane. As will be discussed below, different actuators are disclosed which allow formation of the varying proximal and distal curve configurations.

Figure 2E:
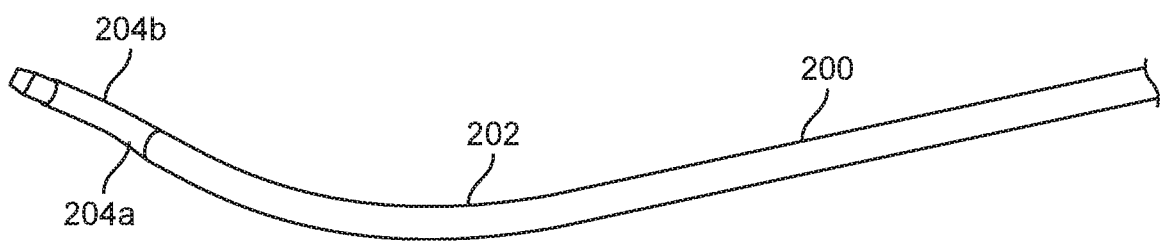

FIG. 2E shows an example where deflecting two or more distal curves simultaneously along with a proximal curve allows the sheath to navigate in an infinite number of planes. Here, proximal curve 200 is formed in a first plane. A first distal curve 204a is then formed in the same plane as the proximal curve 202. A second distal curve 204b is also formed bending the distal end of the sheath out of the first plane into a second plane that is transverse to the first plane. Thus, a complex curve is formed, and this demonstrates that the sheath may navigate an infinite number of planes. The example in FIG. 2E is achieved with one proximal curve and two distal curves, but this may also be accomplished with two proximal curves and one distal curve. Other combinations of curves are possible to provide an infinitely navigable sheath.

Figure 3:
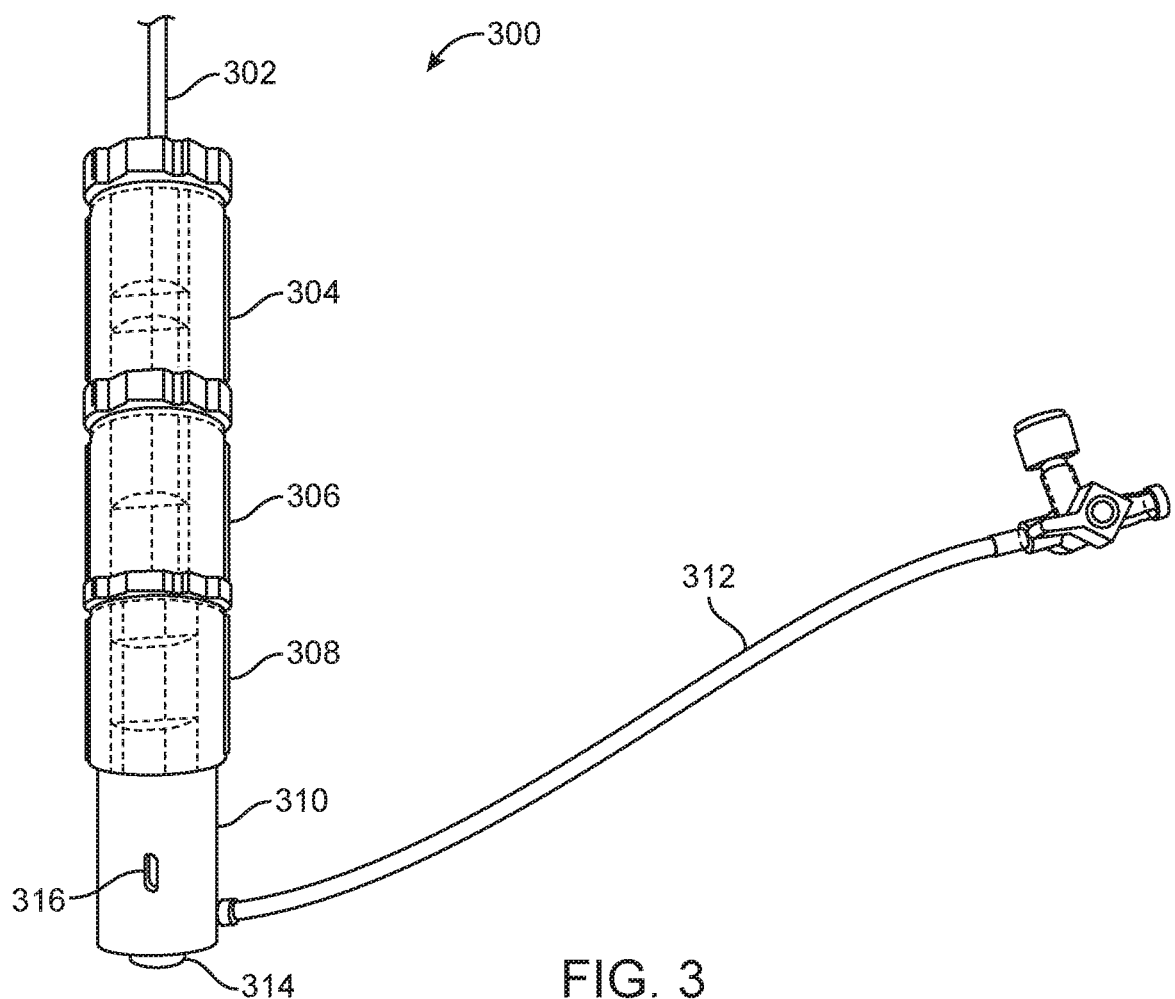
FIG. 3 shows an example of an actuator that may be used to control curves in a steerable sheath.

FIG. 3 shows an example of an actuator that may be used to control curves in a steerable sheath 300. The steerable sheath 300 includes an elongate shaft 302 having a proximal portion, a distal portion (not shown) and an intermediate portion (not shown) between the proximal and distal portions. The proximal portion of the elongate shaft 302 is coupled to handle 310. Handle 310 includes three actuators 304, 306, 308. Here, all three actuators are rotatable wheels. Each wheel is threaded on an internal surface and rotation of the wheel translates the rotational motion to linear motion with a first linear screw (also referred to herein as a shuttle) in the handle as will be discussed in greater detail below. Each actuator may have one pull wire coupled to the shuttle so that rotation of the wheel applies tension to the pull wire which is also coupled to the distal portion or the intermediate portion of the elongate shaft 302 thereby bending the distal portion or the intermediate portion to form the distal curve or the proximal curves described in FIGS. 2A-2E above. An actuator may also have a second linear screw (also referred to herein as a shuttle) that is parallel to the first linear screw. And a second pull wire is then coupled to the second shuttle and also coupled to the distal portion or intermediate portion of the elongate shaft, usually at the same axial position as the first pull wire but circumferentially offset from the connection point of the first pull wire by about 180 degrees on the opposite side. Thus actuation of the first pull wire bends the elongate shaft in a first direction in a first plane and actuation of the second pull wire bends the elongate shaft in the opposite direction in the first plane. Threads on the second shuttle may be opposite of the threads on the first shuttle so that rotation of the wheel moves one shuttle in one direction while the second shuttle moves in the opposite direction thereby simultaneously controlling both pull wires.

The second actuator 306 generally takes the same form as the first actuator 304 and has one or two pull wires that are attached to either the intermediate portion or the distal portions of the elongate shaft, but in this example there are two pull wires each attached to the distal portion of the elongate shaft. Rotation of the second wheel tensions a first pull wire thereby bending the distal portion of the elongate shaft into a distal curve either in the first plane, and rotation of the second wheel in the opposite direction tensions the second pull wire thereby bending the distal curve in the opposite direction in the first plane. The two pull wires are coupled to the distal portion of the elongate shaft and are circumferentially offset from one another, such as 180 degrees offset. Two shuttles are also included, each having opposite threads as the other shuttle so that actuation of the wheel moves the shuttles in opposite directions (one forward and one backwards).

The third actuator 308 generally takes the same form as the first actuator and second actuator 304, 306 and has one or two pull wires that are attached to either the intermediate portion or the distal portions of the elongate shaft, but in this example there are two pull wires each attached to the distal portion of the elongate shaft. Rotation of the third wheel tensions a first pull wire thereby bending the distal portion of the elongate shaft into a distal curve in the second plane, and rotation of the second wheel in the opposite direction tensions the second pull wire thereby bending the distal curve in the opposite direction in the second plane. The second plane may be orthogonal or transverse to the first plane. The two pull wires are coupled to the distal portion of the elongate shaft and are circumferentially offset from one another, such as 180 degrees offset. As well as being circumferentially offset from the two pull wires in the second actuator. Thus, for example, the four pull wires in the second and third actuators maybe coupled to the distal portion of the elongate shaft at the same axial position but circumferentially offset from one another by 90 degrees. This is not intended to be limiting and any angular spacing may be used. Two shuttles are also used, each having opposite threads as the other shuttle so that actuation of the wheel moves the shuttles in opposite directions (one forward and one backwards). Additional figures and details describing actuation of rotatable wheels and pull wires is provided below.

The proximal end of the handle 310 may include a window 316 which allows the operator to see inside the handle to determine if any air bubbles are present. Alternatively, a portion of, or the entire handle assembly can be made from a transparent material that allows the operator to screen for accidental introduction of air bubbles. If so, the air bubbles may be flushed or aspirated out with side port 312 which is fluidly coupled to the elongate shaft lumen. A stopcock (one-way or multi-way) may be coupled to the side port to control fluid flow. A hemostasis valve 314 such as a duck bill valve or a Tuohy-Borst may be used to prevent blood from flowing out of the lumen in the sheath.

Figure 4:
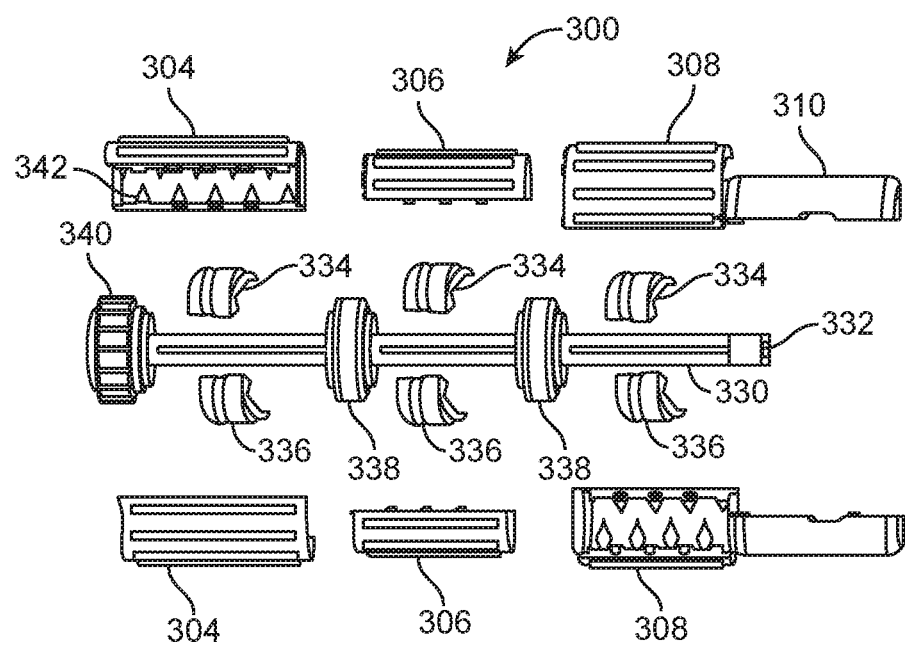
FIG. 4 shows an exploded view of the handle in FIG. 3.

FIG. 4 shows an exploded view of the handle 300 in FIG. 3. Here, actuators 304, 306, 308 have upper and lower rotatable wheel halves which are clamped around the handle. The inner surface of each upper and lower rotatable wheel 304, 306, 308 is threaded so that circular rotation of the wheel is converted into linear motion of each shuttle 334, 336. Here, each actuator 304, 306.308 includes two shuttles and rotation of the wheel moves one shuttle distally while the other shuttle moves proximally. Rotation of the wheel in the opposite direction moves the shuttles in the opposite direction so now one shuttle moves proximally while the other moves distally. The thread may be a standard helical thread, or here the threads are diamond shaped protrusions 342 where the four sides of the diamonds provide inclined surfaces with an inflection so that slope of the incline changes from positive to negative, or negative to positive. Thus, when the diamond shaped protrusions cooperate with the threads on the shuttles, rotation of the wheel will be converted into linear motion of the shuttles along shaft 330. Pull wires (not shown in this figure) are attached to each shuttle and thus movement of the shuttle applies tension or alleviates the tension in the pull wires thereby forming the proximal or distal curves in the elongate shaft. Hubs 338, 340 (here three hubs), have apertures disposed through the hubs and the pull wires may pass through the hubs as will be shown in greater detail in this specification. The hubs also help secure the rotatable wheel. Shaft 330 includes a central lumen 332 that is fluidly coupled with the lumen in the sheath. The proximal portion of the handle 310 may include the window allowing for visualization of bubbles in the lumen (or the transparent handle disclosed above), a side port or hemostasis valve shown in FIG. 3.

Figure 5:
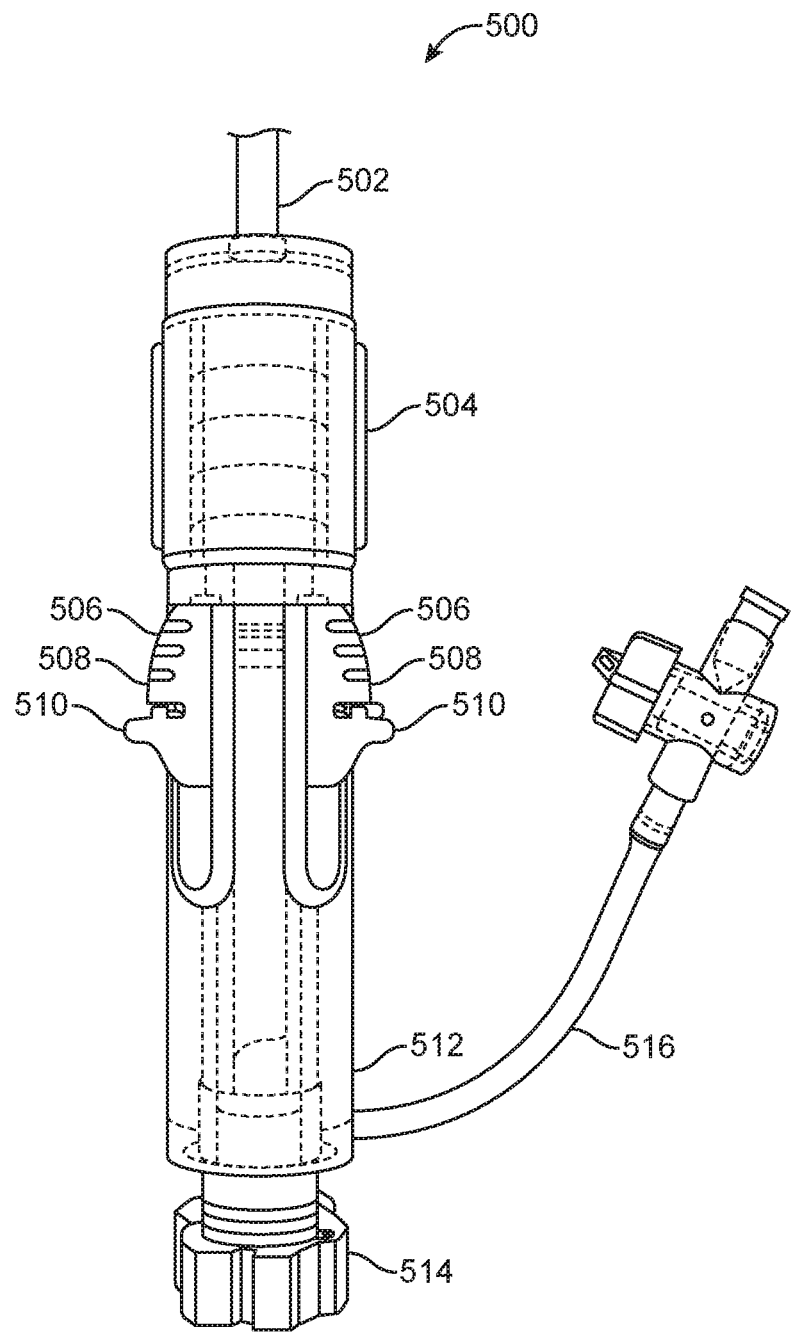
FIG. 5 shows another example of a handle with actuators that may be used to control any steerable sheath.

FIG. 5 shows another example of a handle 500 with actuators that may be used to control any steerable sheath. The handle 500 is coupled to the proximal end 502 of any of the steerable sheaths disclosed herein and actuation of actuators 504, 506 may be used to form any of the proximal or distal curves disclosed herein. The proximal end 512 of the handle may include a side port 516 or a hemostasis valve 514. The side port 516 is substantially the same as previously disclosed and includes a short length of tubing that is coupled to the proximal end of the handle 500 and is fluidly coupled to the lumen of the elongate shaft of the steerable sheath to permit the introduction of fluids into the lumen, or removal of fluids from the lumen. A one-way or multi-way stopcock may be coupled to the free end of the side port tubing in order to control fluid flow. The hemostasis valve 514 may be a duckbill valve. Tuohy-Borst valve, or other valve that permits introduction of a catheter or other device into the handle while controlling fluid flow out of the proximal end of the handle, such as blood. The hemostasis valve may also be used to help hold the guidewire or elongate shaft in the handle and prevent movement when the hemostasis valve is tightened, e.g. when using a Tuohy-Borst valve.

The distal-most actuator 504 may be an actuatable wheel that an operator rotates to control the proximal curve on the steerable sheath. Similar to the example in FIG. 4, rotational movement of the actuatable wheel is converted into linear motion of one, two, or more shuttles which are attached to pull wires connected to the intermediate portion of the elongate shaft. Thus, rotation of the wheel in a first direction will tension a first pull wire and form the proximal curve along the intermediate portion of the steerable sheath in a first direction and in a first plane, while rotation of the wheel in the opposite direction releases the tension on the frst pull wire allowing the proximal curve to return to an unbiased configuration and further actuation of the wheel then applies tension to the optional second pull wire (if there is a second shuttle) which then forms the proximal curve in a second direction opposite the first direction, and in the same first plane. Additional disclosure related to pull wire configurations and attachment to the steerable sheath is provided below.

An additional actuator 506 is also coupled to the handle, and in this example, there are four additional actuators 506. Two are visible and the other two are not visible in this view. Here the actuators 506 include a textured distal ramp portion 508 on the distal end of the actuator and proximal ramp portion 510 that is pivotably coupled with the distal ramp portion 508. Pushing the proximal ramp portion 510 distally lifts the proximal-most end of the proximal ramp portion 510 up and away from a rack disposed in the handle and not visible in this view. This disengaging a tooth coupled with the proximal ramp portion from the rack and allows the slider to be advanced distally. Distal advancement allows release of tension in a pull wire coupled to the slider and the distal portion of the elongate shaft of the steerable sheath, thereby returning the distal curve to an unbiased configuration.

Proximal retraction of the proximal ramp portion 508 draws the slider proximally along the rack since the tooth is curved to form a cam surface that easily glide over the rack when proximally retracted. Proximal retraction of the proximal ramp portion 508 moves the slider proximally which applies tension to the pull wire connected to that slider, which then forms a distal curve in the distal portion of the elongate shaft of the steerable sheath. This curve may be in the same first plane as the proximal curve, or it may be in a second plane that is transverse or orthogonal to the first plane. A second slider may be disposed on the handle circumferentially offset so it is roughly 180 degrees offset and the second slider may be used to form the distal curve in the opposite direction as the first direction and in the same plane. Two additional sliders may also be included on the handle to form the distal curve in either a first direction or a second direction opposite the first direction and either in the first plane or in the second plane that is transverse or orthogonal to the first plane. Thus, for example, if there are four sliders, two sliders form the distal curve in first or second opposite directions, in the first plane (the same plane as the proximal curve), and the other two sliders form the distal curve in a first or second opposite direction, in the second plane orthogonal or transverse to the first plane. Each slider is attached to a pull wire so there would be four pull wires and they may be coupled to the distal portion of the elongate shaft of the sheath at circumferentially offset positions, for example every ninety degrees, with cooperating pairs of pull wires offset 180 degrees. In addition, deflecting two or more of the distal curves simultaneously along with a proximal curve allows the sheath to navigate an infinite number of planes, as seen in FIG. 2E above. Or, deflecting two or more proximal curves simultaneously with one distal curve also allows an infinitely navigable sheath.

Figure 6:
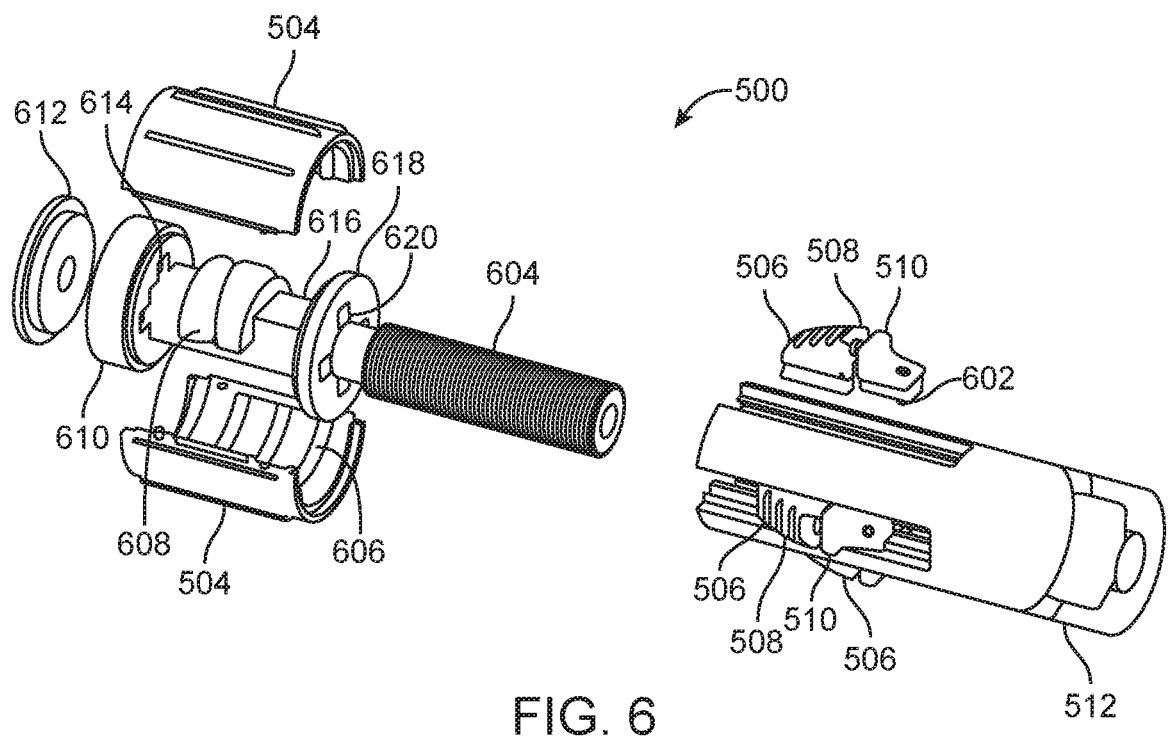
FIG. 6 shows an exploded view of the handle in FIG. 5.

FIG. 6 shows an exploded view of the handle 500 in FIG. 5 and more clearly illustrates operation of the actuators. As previously disclosed, the handle 500 includes sliders 506 with proximal and distal portions 510, 508 for locking, unlocking, advancing, and retracting of the slider along a rack 604 with teeth. A tooth 602 on the bottom of the proximal portion 510 engages the teether on the rack 604. When the proximal portion 510 of the slider is pushed distally, this lifts up the proximal portion of the slider and disengages tooth 602 from the teeth on the rack 604. A spring disposed between the proximal and distal portions is biased to push the proximal portion back down so that the tooth 602 engages the teeth in the rack 604 to lock the slider and prevent distal movement. This is described in more detail below. Here, the handle 500 includes four sliders. Two sliders are visible and the other two are not visible in this view. The sliders slide along channels in the handle body to ensure smooth linear motion. A pull wire is attached to each slider and the pull wire then extends distally along the handle, through holes 620, 614 in the hubs 618, 610 and the distal ends of the pull wires are coupled to the distal portion of the elongate shaft.

The distal-most actuator includes a rotatable wheel 504 that is in two halves disposed around the shuttle 608 (also referred to as a lead screw) which converts rotational motion to linear motion. Threads 606 on the inner surface of the wheel 504 engage cooperating threads on the shuttle 608 which slides over shaft 616 which has a square or rectangular cross-section. Because the shuttle cannot rotate around the shaft 616, rotation of wheel 504 is converted into linear motion of shuttle 608 along shaft 616. A pull wire is attached to the distal portion of the shuttle and may pass through an aperture 614 in the hub 610 and the free end of the pull wire is then coupled to the intermediate portion of the elongate shaft of the steerable sheath. Hubs 618, 610 constrain the rotatable wheel so that it can only rotate and prevent linear motion of the wheel. The hubs 618, 610 also help secure the components together. Apertures 620, 614 in the hubs 618, 610 allow pull wires to pass through the hubs unobstructed and also prevent entanglement of the pull wires. A distal cap 612 seals the distal end of the handle. Extending proximally from the shaft 616 is a cylindrical rod with teeth that acts as a rack 604 over which the sliders move. The tooth 602 on each slider 506 when engaged with the teeth on the rack prevent the slider from moving distally which locks the slider in position thereby holding tension in the pull wire and holding the curve formed by that pull wire. Proximal movement is not inhibited by engagement of the tooth with the teeth on the rack. This locking mechanism is described in greater detail below. FIG. 6 shows the rotatable wheel with only a single shuttle 608, however this is not intended to be limiting and a second shuttle may be added to control a second pull wire coupled to the intermediate portion of the elongate shaft of the sheath. The thread on the second shuttle may be opposite of the first shuttle threads so that rotation of the wheel will move one shuttle proximally while the second shuttle moves in the opposite direction, distally. Or, the shuttle threads may be the same so both shuttles move in the same direction when actuated by the wheel.

Figure 7:
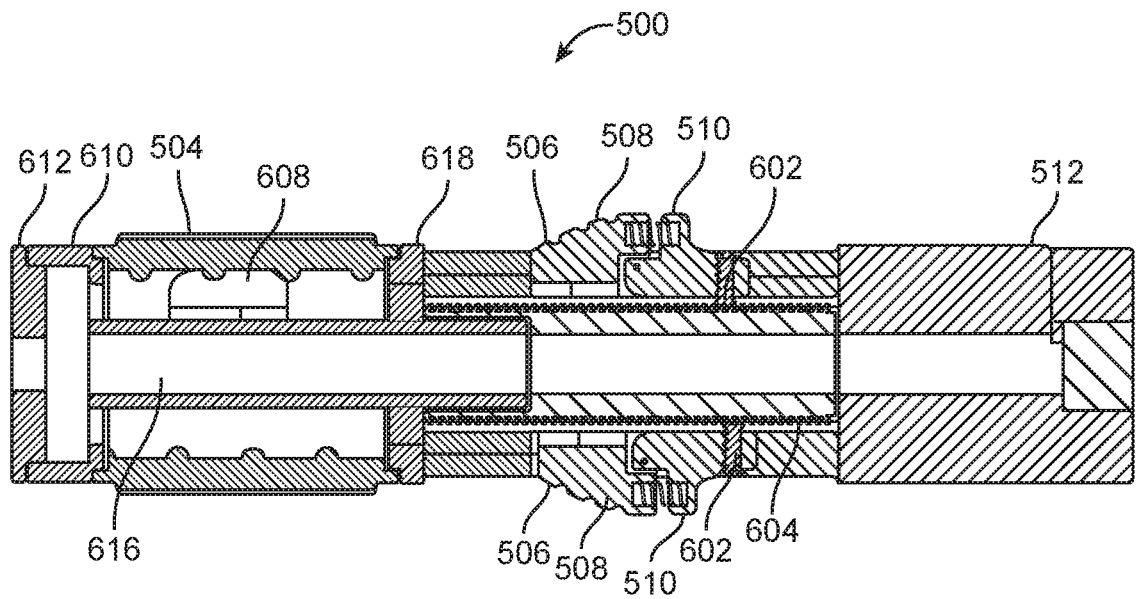
FIG. 7 shows a side view of the handle in FIG. 6.

FIG. 7 shows a side view of the handle 500 in FIG. 6 and operates in the same manner are previously described. FIG. 7 shows the single shuttle 608 and also shows engagement of the tooth 602 with the teeth on the rack 604. The two sliders 506 are also shown circumferentially offset from one another, here 180 degrees offset which may be helpful to the operator as an indicator of the direction in which each slider controls bending, although this is not intended to be limiting and sliders may be spaced in any desired configuration.

Figure 8A:
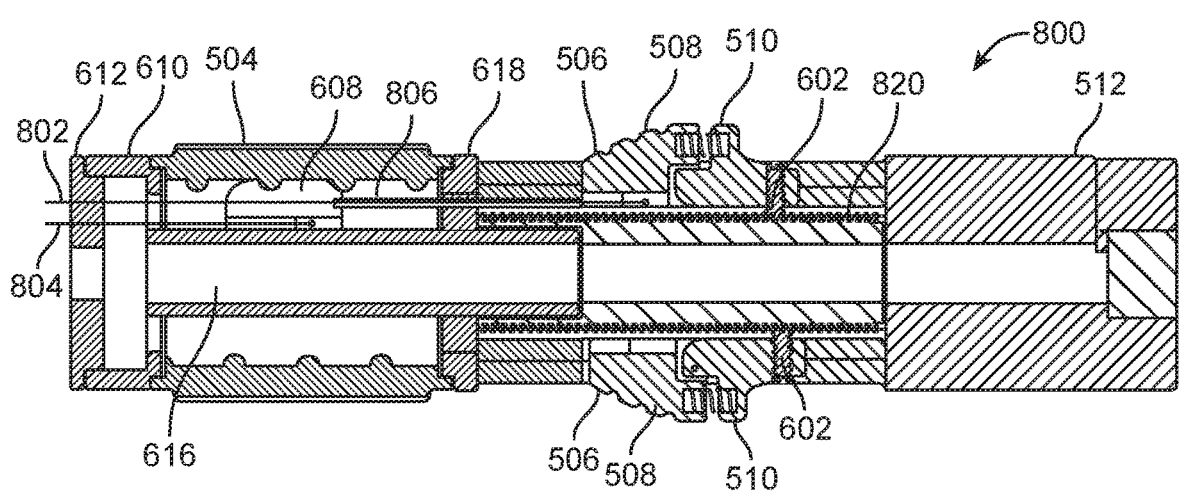
FIGS. 8A-8C shows an example of an anti-slack mechanism.
Figure 8B:
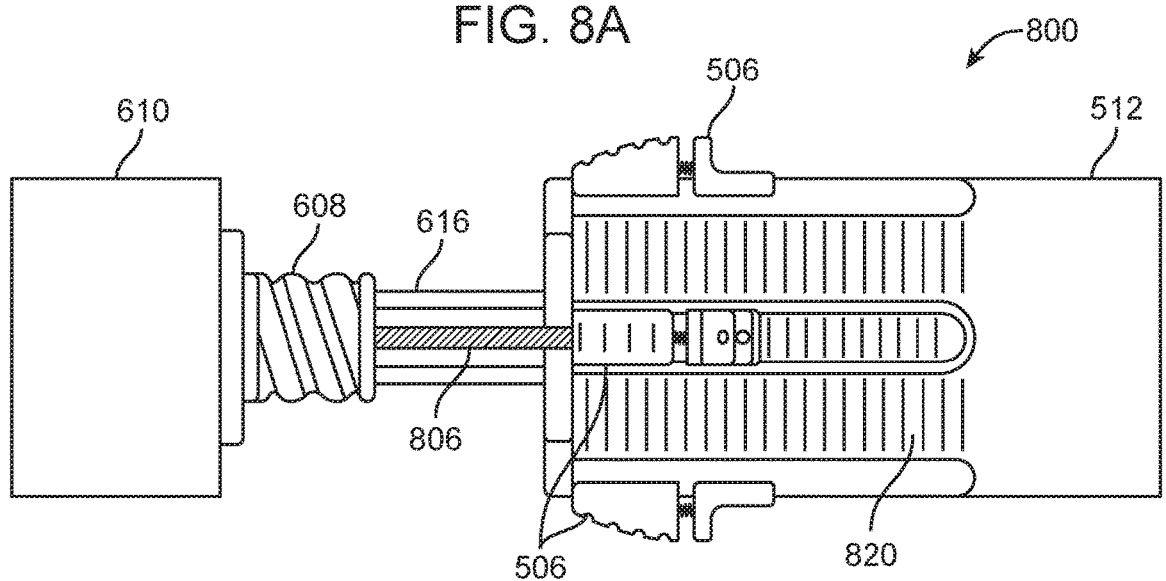
Figure 8C:
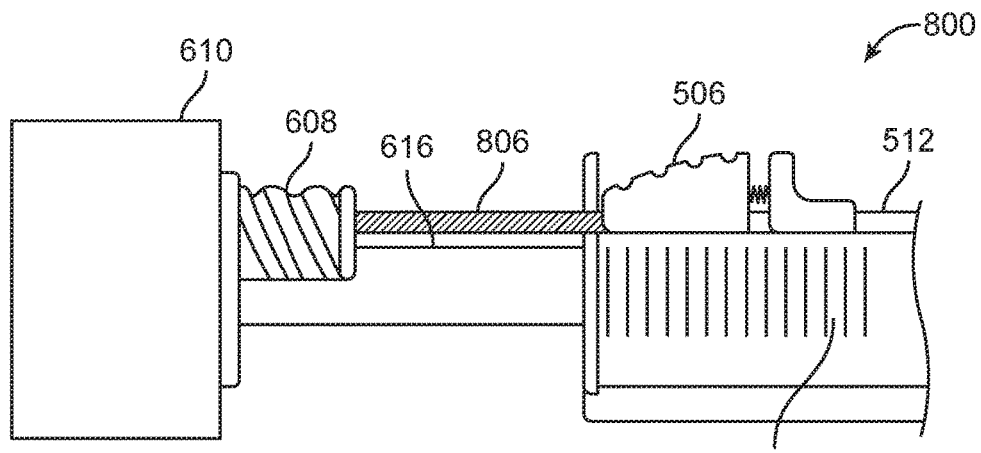

FIGS. 8A-8C show another example of a handle similar to the handle in FIGS. 6-7 but with the major difference being the addition of an optional anti-slack feature. Because actuation of the rotatable wheel forms a curve in one portion of the elongate shaft of the steerable sheath, for example in the intermediate portion, the shaft forms a radiused curve which results in slack in the pull wires coupled to the sliders. When the sliders are actuated, they must be moved first to take up the excess slack before they can tension their respective pull wires and form curves to the other portions of the elongate shaft of the steerable sheath. Therefore, addition of an anti-slack feature removes slack from the slider pull wires as the rotatable wheel actuates its pull wire and thus actuation of the sliders maintain close correspondence with the formation of the curves in the steerable sheath and do not require slack to be removed.

FIG. 8A shows the distal-most actuator includes the rotatable wheel 504 with the moving shuttle 608 that slides along shaft 616. The handle 800 also includes sliders 506 with proximal and distal slider portions 508, 510 and the locking tooth 602 which releasably engages the teeth 820 in the rack. Operation of the distal-most actuator and the sliders is the same as previously described above in FIGS. 6-7. The slack mechanism includes a pusher 806 such as a tube like a hypotube or other tube that is coupled to the proximal end of the shuttle 608. The pull wire connected to the slider may pass through the hypotube 806 freely so as not to hinder actuation of the distal curve. As shuttle 608 moves proximally, the pusher 806 abuts the distal end of the slider 506 and continued proximal movement of the shuttle correspondingly pushes slider 506 proximally thereby eliminating any slack in the pull wire coupled to that slider. Thus, when that slider is retracted proximally to tension its respective pull wire, tension is applied immediately since there is no slack in the pull wire and control of the resulting curve corresponds tightly with actuation of the slider. When the shuttle is moved distally in the opposite direction, the pusher 806 disengages from the slider and the slider may be moved distally. This anti-slack feature maybe used in any of the handle examples disclosed herein. FIG. 8A only shows two sliders but may include four total sliders and the other two are not seen in this view. Additionally, only a single shuttle is shown with the anti-slack feature, but a second shuttle may also be added with or without the anti-slack feature. Also, the anti-slack feature may include two pushers per shuttle to abut and push two sliders and thus when there are two shuttles, slack may be avoided in all four pull wires coupled to the sliders. The pull wire 802 coupled to the slider may extend through a channel or lumen in the pusher and pass as described previously through apertures in the hubs 618, 610, and the shuttle. Pull wire 804 is coupled to the shuttle 608 and may pass through an aperture in the shuttle and the distal hub 610. Other aspects of FIG. 8A are generally the same as the handle in FIGS. 6-7.

FIG. 8B shows a top view of the handle in FIG. 8A and highlights the pusher 806 coupled to the proximal end of the shuttle 608 and the pusher 806 abutted with slider 506. Here, a single pusher is shown, but one of skill in the art will appreciate that a pusher may be coupled to each shuttle to push the corresponding slider. Also in this view, the rotatable wheel is removed to highlight the shuttle 608. Other aspects of FIG. 8B are the generally the same as in FIG. 8A.

FIG. 8C shows a side view of the handle 800 in FIGS. 8A-8B. Other aspects of the handle are generally the same as in FIGS. 8A-8B.

Figure 9A:
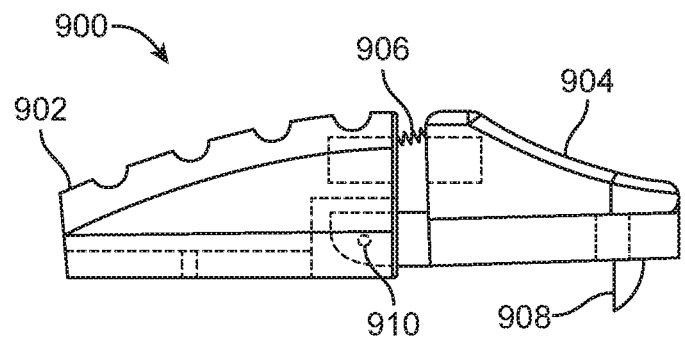
FIGS. 9A-9D show an example of a slider.

FIGS. 9A-9D show an example of a slider that may be used in any of the handles disclosed herein. FIG. 9A shows the slider 900 which includes a proximal slider portion 904, a distal slider portion 902, a spring 906, a tooth 908, and a hinge or pivot 910. As previously discussed above, the proximal portion 904 includes a ramped portion that is configured for easy actuation by a thumb or finger and controls the locking of the slider. The distal portion 902 also includes a ramped portion that may be textured or knurled so that a finger or thumb may easily grasp and move the proximal slider portion. A hinge or pin and pivot 910 couples the two halves of the slider together and so they are able to pivot relative to one another. A spring 906 is coupled to both portions of the slider and is biased to push the two halves away from one another so both slider halves are flat and generally colinear with one another. This ensures that tooth 908 engages the teeth on the rack in the handle. The tooth 908 includes a flat distal face that prevents distal actuation of the slider mechanism unless the proximal slider portion 904 is pushed distally causing the proximal end of the proximal slider portion 904 to pivot upward slightly, enough that the tooth 908 disengages from the teeth in the rack and allows the slider to be advanced distally. The tooth 908 also has a curved shape on the proximal end that acts as a cam so that when the slider is pushed proximally, the cam will slide smoothly over the teeth in the rack and proximal movement of the slider is not prevented.

Figure 9B:
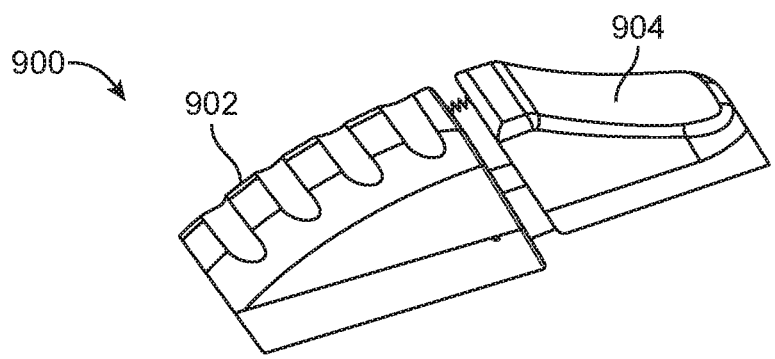

FIG. 9B shows a perspective view of the slider in FIG. 9A.

Figure 9C:

FIG. 9C shows an example of the teeth on rack 920 in any of the handles disclosed herein, and which tooth 908 on the slider may engage. The teeth have an angled leading edge which allows the cammed surface of tooth 908 to slide easily over during proximal retraction of the slider, and a vertical trailing edge that engages the slider and prevents distal slider movement unless the tooth is disengaged from the teeth on the rack as disclosed above with respect to FIG. 9A.

Figure 9D:
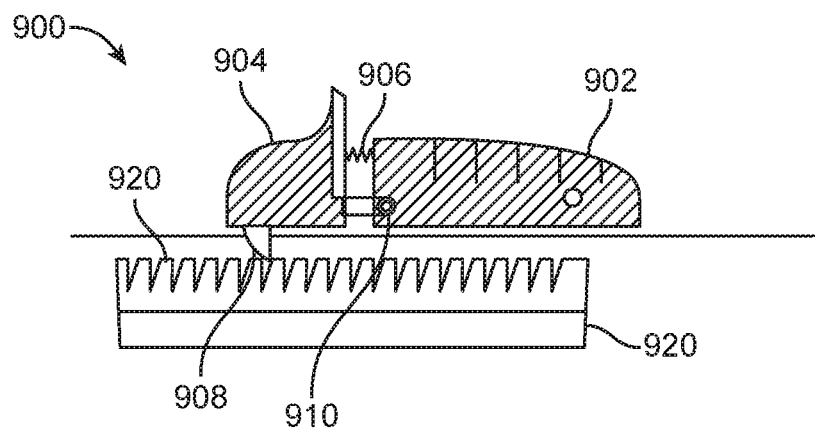

FIG. 9D shows the slider 900 engaged with the teeth 920 on the rack 920.

Figure 10A:
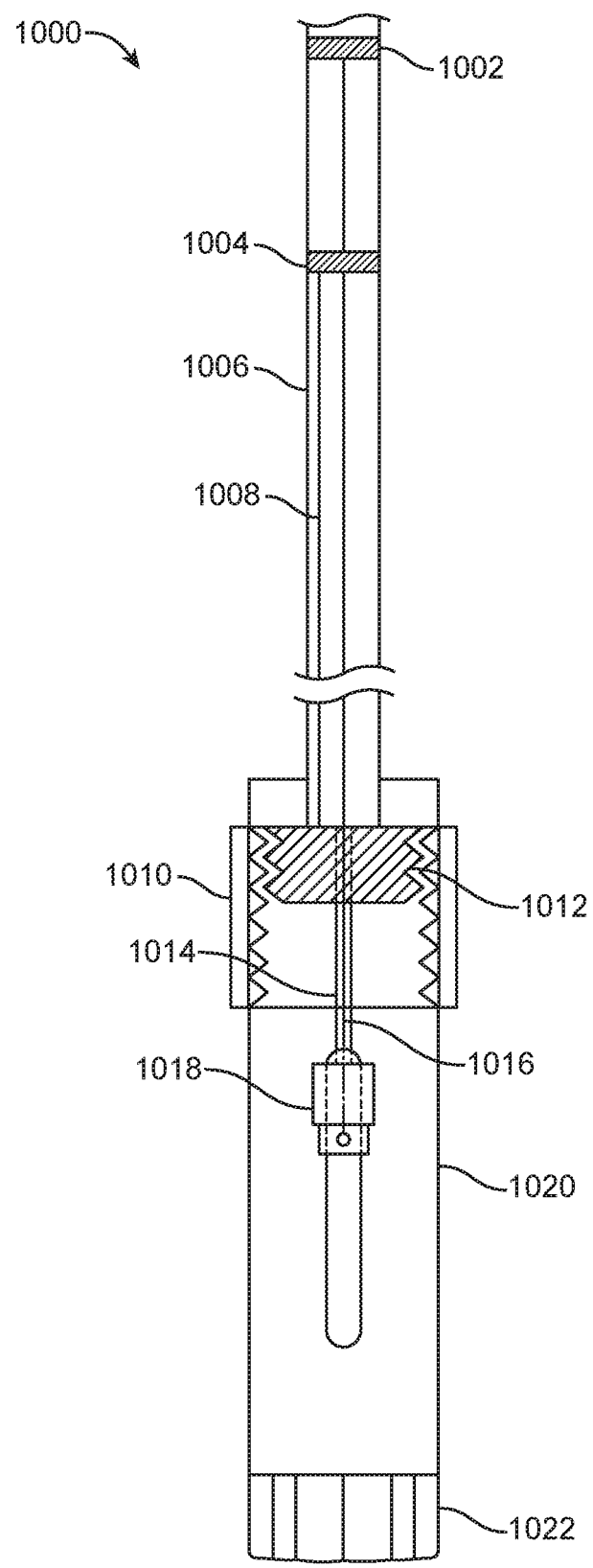
FIGS. 10A-10B show an example of actuation of a steerable sheath.
Figure 10B:
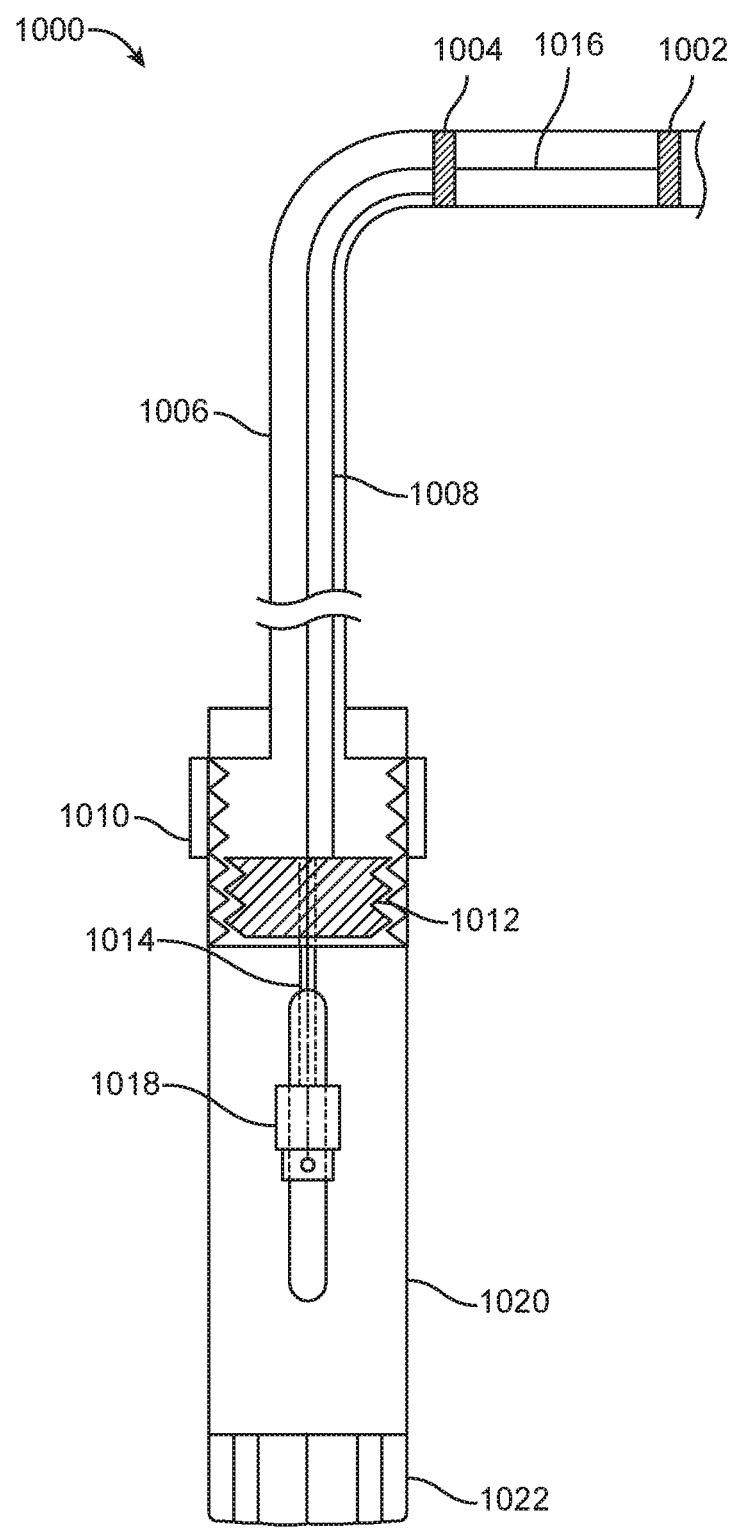

FIGS. 10A-10B show an example of actuation of a steerable sheath, using a rotatable wheel actuator and a slider actuator, such as disclosed in FIGS. 5-7. In FIG. 10A the steerable sheath 1000 include an elongate shaft 1006 having a lumen and a handle 1020. The proximal end of the elongate shaft 1006 is coupled to the handle 1020. The handle 1020 includes two actuators such as a rotatable wheel 1010 and a slider 1018. A hemostasis valve 1022 such as a duckbill valve or a Tuohy-Borst valve may be included on the proximal end of the handle to prevent fluid leakage as well as securing guidewires, catheters, or other elongate instruments that maybe slidably disposed in the lumen of the steerable sheath. A proximal ring 1004 and a distal ring 1002 are coupled to the elongate shaft and serve as a connection point for the pull wires. For example, here distal ring 1002 is coupled to a distal portion of the elongate shaft and proximal ring 1004 is coupled to an intermediate portion or middle portion of the elongate shaft that is disposed between the proximal and distal portion of the elongate shaft. A pull wire 1016 is coupled to the distal ring 1002 and the slider 1018 and another pull wire 1008 is coupled to the proximal ring 1004 and the shuttle 1012. Rotation of the rotatable wheel 1010 is translated into linear motion of shuttle 1012. Thus actuation of the rotatable wheel controls the bending of the intermediate portion of the elongate shaft to form a proximal curve, and actuation of the slider controls the bending of the distal portion of the elongate shaft to form the distal curve. Additionally, a pusher 1014 is also coupled with the shuttle 1012 so that as shuttle 1012 moves proximally it moves pusher 1014 proximally and abuts slider 1018 pushing the slider back in cooperation with rotation of the wheel 1010. Thus, as tension in pull wire 1008 is increased and the proximal curve is formed, any slack that results in pull wire 1016 is taken up because the slider is pushed proximally by the pusher 1014. So when slider 1018 is actuated, the slider will not require proximal retraction to take up slack before the pull wire controls the distal curve. Actuation of the slider will result in immediate response of the distal curve. The example in FIG. 10A only shows a single shuttle but one of skill in the art will appreciate that two or more shuttles may be used as previously disclosed above. Additionally, FIG. 10A also only shows a single slider but this is not intended to be limiting and two, or three, or four, or more sliders maybe used to control the distal curve in any number of other directions, such as in FIGS. 5-7. Alternatively, by controlling multiple sliders at various locations allows the sheath to steer in any number of other directions.

FIG. 10B shows actuation of the rotatable wheel 1010 to move the shuttle 1012 proximally thereby forming the proximal curve in the intermediate portion of the elongate shaft 1006 of the steerable sheath. If a second shuttle is included with the rotatable wheel 1010, actuation of the wheel in the opposite direction would form the proximal curve in the opposite direction but in the same plane, if a second pull wire (not illustrated) was coupled to the proximal ring at a position circumferentially offset from the first pull wire, approximately 180 degrees offset. FIG. 10B also shows the pusher 1014 abutted with the slider and pushing the slider proximally to remove slack from pull wire 1016. The slider may be the same as in FIGS. 9A-9D with the lock to prevent unwanted movement.

Figure 11:
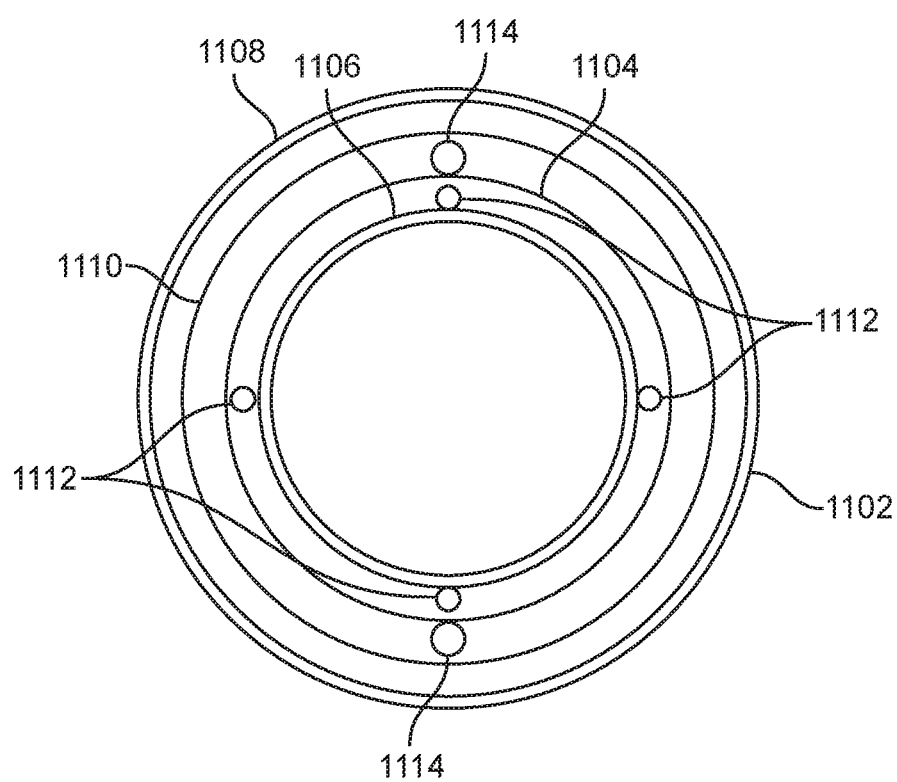
FIG. 11 shows an example of a cross-section of an elongate shaft in a steerable sheath.

FIG. 11 shows a cross-section of the steerable sheath elongate shaft 1102. The elongate shaft 1102 may be formed from several layers of material, for example the inner-most layer 1106 which forms the lumen for the steerable sheath may be a polytetrafluoroethylene (PTFE) layer of tubing to provide a smooth surface. Next, one, or two, or three, or four, or more small diameter tubes 1112 such as polyimide or PTFE tubes are disposed over the surface of the inner-most layer 1106 and these tubes form the lumens for the distal curve pull wires. The number of tubes used is dependent on how many pull wires are used. Here, four tubes are used in order to accommodate four pull wires. The tubes are spaced approximately every 90 degrees, but this is not limiting and any desired spacing may be used. An inner braid layer 1104 is then disposed over the tubes 1112, then one or two, three, four, or more other small diameter tubes 1114 such as polyimide, PTFE, or other fluoropolymer tubes are disposed over the inner braid 1104. Tube 1114 provide the lumens for the proximal curve pull wires and here there are two tubes 1114 circumferentially offset by 180 degrees. Any positioning may be used, and the number of tubes is dependent on the number of proximal curve pull wires. An outer braid 1110 is disposed over the proximal curve pull wires and a final outer polymer layer 1108 is disposed over everything. Thus, each pull wire is slidably disposed in a separate lumen in order to ensure that actuation of each pull wire is smooth, and friction is reduced as well as avoiding entanglement of the pull wires.

Figure 12:
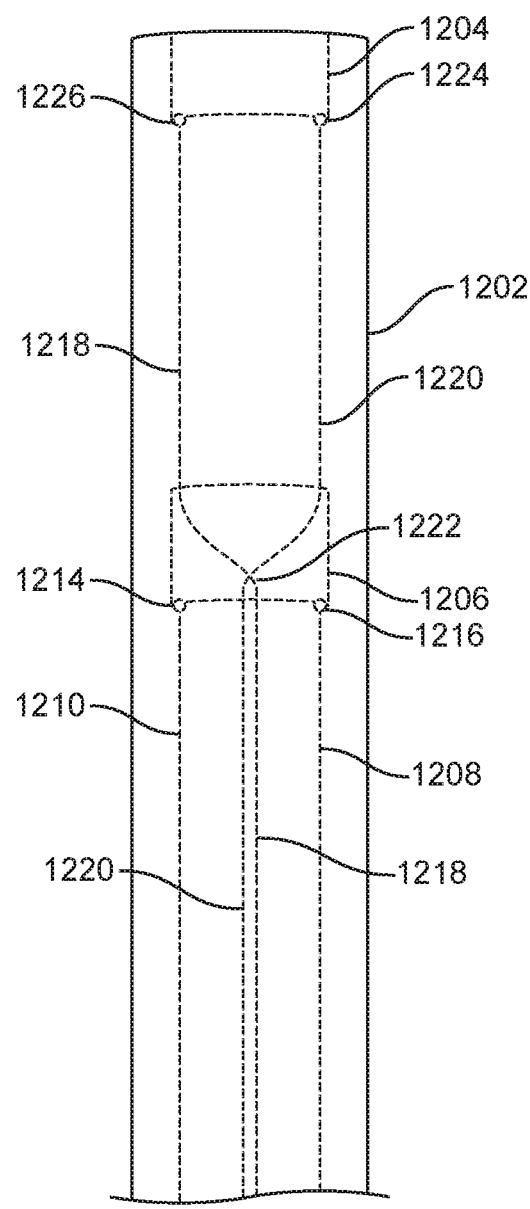
FIG. 12 shows an example of pull wire routing in a sheath.

FIG. 12 shows an example of how pull wires may be routed through an elongate shaft 1202 of any of the steerable sheaths disclosed herein as a way of addressing slack in some pull wires that may result when the sheath is curved into different configurations. The pull wires may be routed in a linear fashion through the elongate shaft and parallel with the longitudinal axis of the elongate shaft, or in any of the examples the pull wire routing may be altered to minimize slack Pull wire ring 1204 is coupled to a distal portion of the elongate shaft to control the distal curve, and pull wire ring 1206 is coupled to the intermediate portion of the elongate shaft to control the proximal curve.

In the case where the proximal bi-directional curve is in the plane of the page, the two pull wires 1218, 1220 that control the distal curve in the same plane will experience slack or tension. In order to prevent this from happening, these pull wires 1218, 1220 are routed through the channel in the proximal pull wire ring 1206. The distal curve in-plane pull wires 1218, 120 are then circumferentially offset from their original axis and re-routed along a path that defines a plane orthogonal or transverse to the plane of the proximal curve. This may be accomplished by offsetting the pull wires 11218, 1220 by about 90 degrees from their initial axis. When the proximal curve is actuated, slack or tension in the rerouted pull wires is therefore minimized.

In this example, two pull wires 1208, 1210 run linearly and parallel with the elongate shaft and both are coupled to pull wire ring 1206 which is proximal of pull wire ring 1204. The connection points 1214, 1216 are circumferentially offset by about 180 degrees in this example. Two additional pull wires 1218, 1220 also run linearly and parallel with the longitudinal axis of the elongate shaft but then the pull wires 1218, 1220 are rerouted 1222 adjacent pull wire ring 1206. Both pull wires then continue to run linearly and parallel with the elongate shaft until they are attached 1224, 1226 to pull wire ring 1204 which is distal of pull wire ring 1206. The connection points are circumferentially offset from one another by about 180 degrees. Re-routing pull wires may help control tension and slack in the pull wires and may provide better control of deflection and bending.

Figure 13:
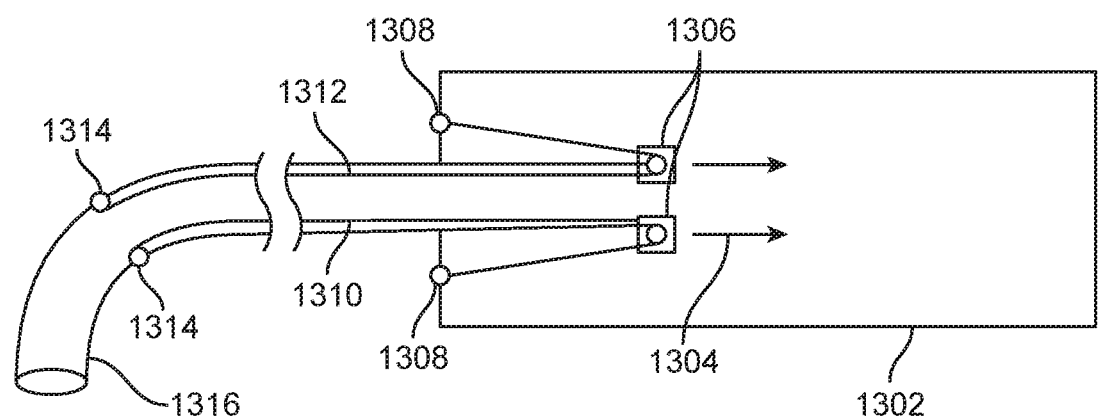
FIG. 13 shows an example of a pulley.

FIG. 13 shows an example of the use of a pulley to facilitate manipulation of a pull wire in any of the examples of a steerable sheath disclosed herein. An elongate shaft 1316 is coupled to a handle 1302. Pull wires 1310, 1312 are coupled 1314 to the elongate shaft and also the handle 1308. A pulley 1306 is operatively coupled to the pull wires 1310, 1312 thereby providing mechanical advantage when the pulleys are actuated as indicated by arrows 1304. Use of the pulley configuration allows highly responsive deflection with short actuation. In some examples the ratio of deflection to actuation is greater than 1:1, while in other examples the ratio may be less than 1:1. This example shows two pull wires with a pulley, however this is not intended to be limiting and one pull wire may have a pulley while the other pull wire may not have a pulley. And in examples having more than two pull wires, a pulley may be used with any number of those pull wires.

Figure 14A:
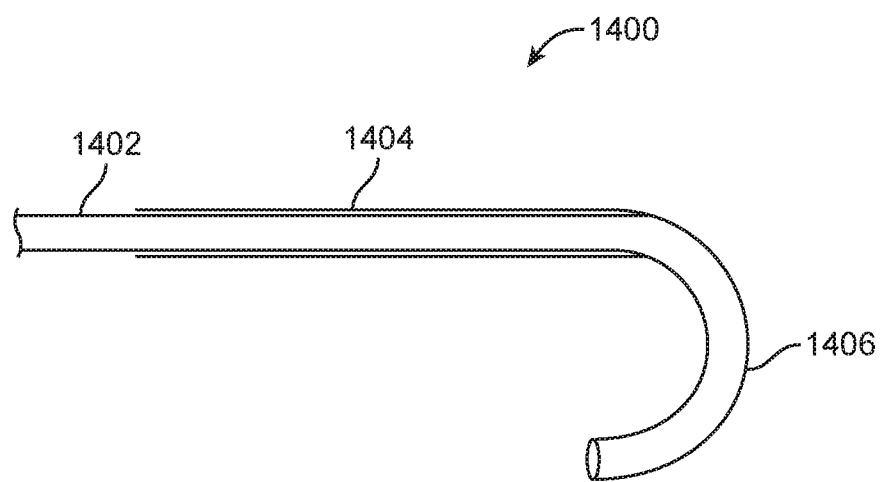
FIG. 14A-14B show an example of a variable curve sheath.
Figure 14B:
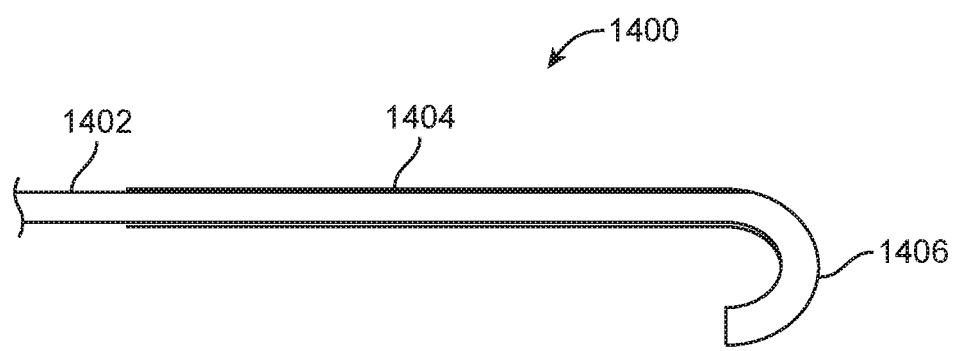

FIGS. 14A-14B show an example of a variable curve sheath 1400. The device includes an inner stiff shaft 1402 slidably disposed in the sheath 1404. A curve is pre-set in the inner shaft 1402. As the inner shaft 1402 is advanced through the outer sheath 1404 and the distal portion of the inner shaft 1402 becomes unconstrained by the outer sheath 1404, the distal portion of the inner shaft 1402 will begin to bend into its unbiased natural curve 1406. The radius of curvature of the curve 1406 depends on how must of the distal portion is exposed. In FIG. 14A, a relatively large portion of the distal end of the inner shaft is unconstrained therefore the curve will have a relatively large bend radius. In FIG. 14B, a relatively shorter section of the distal end of the inner shaft is unconstrained therefore the curve will have a relatively small bend radius. Once the desired bend is formed, a catheter or other diagnostic or interventional device may be inserted into a lumen in the inner shaft and the curve will facilitate delivery to the target treatment area. A handle may be coupled to the inner and outer shaft and sheath to help control relative motion. The variable curve sheath may be used with any of the other actuation mechanisms to further control the curves in the steerable sheath.

Figure 15A:
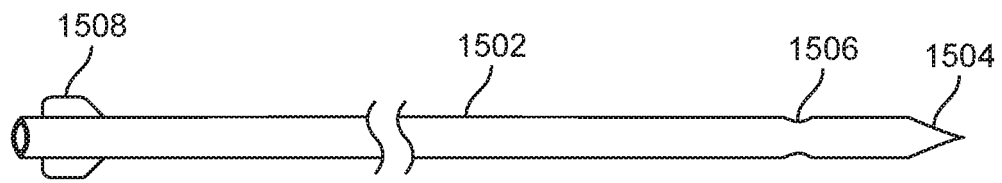
FIGS. 15A-15B show an example of a dilator.
Figure 15B:
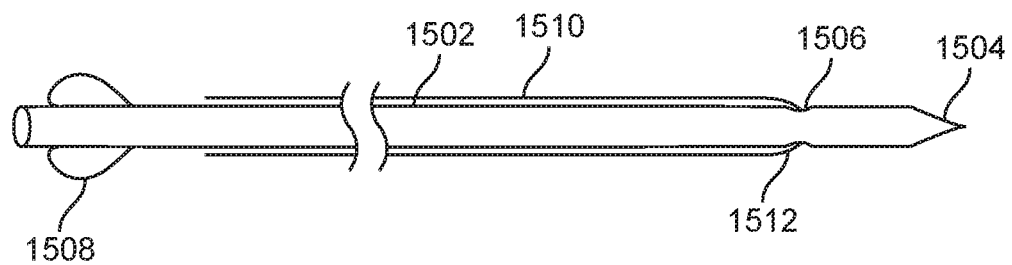

FIGS. 15A-15B illustrate a dimpled dilator that may be used with any of the steerable sheaths disclosed herein. In FIG. 15A, the dilator 1502 includes an elongate shaft with a tapered distal atraumatic tip 1504 and a hub or other connector on the proximal end 1508 of the dilator. A dimple or annular groove 1506 disposed circumferentially around a distal portion of the dilator provides a receptacle for receiving the distal tip of the steerable sheath resulting in a better, smoother dilator-sheath transition.

FIG. 15B the dilator 1502 is inserted into any of the steerable sheaths disclosed herein. The distal tip of the steerable sheath is formed of a resilient material that is biased to collapse into a smaller diameter than the diameter of the main section of the sheath. Therefore, as the dilator is slidably advanced through a lumen in the sheath, the distal end 1512 of the sheath is forced to remain in its larger diameter configuration. However, when the dilator is advanced far enough that the distal end of the sheath 1512 reaches the annular groove 1506, the distal end of the sheath 1512 will collapse into its unbiased smaller diameter and collapse into the annular groove, thereby shielding the leading edge of the sheath in the groove and providing a smooth transition from the dilator to the sheath, without a bump or discontinuous transition.

Figure 16:
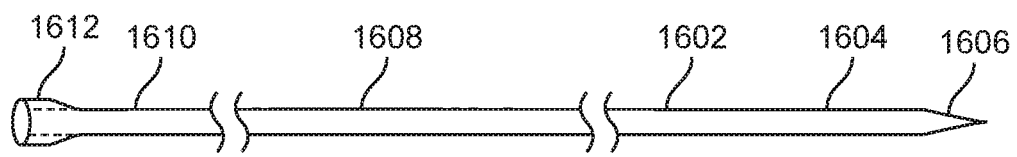
FIG. 16 shows an example of a variable stiffness dilator.

FIG. 16 shows an example of a variable stiffness dilator which may be used with any steerable sheath disclosed herein. Dilator 1602 includes a tapered distal atraumatic tip 1606 and a hub or other connector 1612 on the proximal end. The elongate shaft of the dilator may be divided up into a proximal portion 1610, a distal portion 1604, and a middle or intermediate portion 1608 disposed between the proximal and distal portions. The dilator may be manufactured so that the elongate shaft has any desired stiffness profile along the elongate shaft. For example, the intermediate portion 1608 may be softer and more resilient than the proximal or distal portions 1610, 1604. When the dilator is inserted in any of the steerable sheaths disclosed herein, the softer intermediate portion will therefore bend and flex more easily as the steerable sheath is bent. The proximal portion may be the stiffest in order to give the dilator pushability during delivery, while the distal portion may be the same stiffness as the proximal portion, of it may be softer if desired, or otherwise tailed in order to provide adequate rigidity to push against tissue without causing unwanted trauma to the tissue. Any durometer may be used in the proximal, distal or intermediate portions of the dilator shaft. Thus, the steerable sheath maybe steered with a dilator disposed in the steerable sheath.

In any example of steerable sheath disclosed herein the pull wires may be made from any number of different materials. For example, round or flat metal wires such as stainless steel, or high strength polymer filaments may be used, such as Kevlar.

In any example of steerable sheath disclosed herein the braided layer (such as in FIG. 11) may be made from any number of different materials. For example, round or flat metal wires such as stainless steel or Nitinol to avoid kinking. Alternately, high strength monofilament polymer such as polyether ether ketone (PEEK) or multifilament such as Kevlar and Vectran can be used to be non-magnetic.

In any example of steerable sheath disclosed herein, the sheath may have any diameter or length. For example, sheaths ranging from 8.5 to 15.5 French may be used. Similarly the radius of curvature of the proximal and distal curves may be any radius needed for a particular procedure or anatomy.

In any example of steerable sheath disclosed herein, any of the actuators may include indicia such as printing, markings, colors to indicate to the operator which actuator controls which direction of the which curve.

In any example of steerable sheath disclosed herein, the proximal portion and distal portions of the elongate shaft of the steerable sheath may have any desired length and this maybe based on the procedure being performed or the anatomy. For example, the distal portion of a steerable sheath may have a distal portion where the distal curve is formed, and the distal portion may be the distal-most 2-4 centimeters of the elongate shaft. Similarly, the intermediate portion of the elongate shaft where the proximal curve is formed maybe be the next 4-10 centimeters of the elongate shat that are proximal of the distal portion.

NOTES AND EXAMPLES

The following, non-limiting examples, detail certain aspects of the present subject matter to solve the challenges and provide the benefits discussed herein, among others.

Example 1 is a steerable sheath comprising: an elongate shaft comprising a proximal portion, a distal portion, an intermediate portion disposed between the proximal portion and the distal portion, and a lumen extending between the proximal and distal portions; a first pull wire having a proximal end and a distal end, the first pull wire extending along the elongate shaft; a second pull wire having a proximal end and a distal end, the second pull wire extending along the elongate shaft; a handle coupled with the proximal portion of the elongate shaft; a first actuator disposed on the handle; and a second actuator disposed on the handle, wherein the distal end of the first pull wire is coupled to the intermediate portion of the elongate shaft and the proximal end of the first pull wire is coupled to the first actuator, wherein the distal end of the second pull wire is coupled to the distal portion of the elongate shaft and the proximal end of the second pull wire is coupled to the second actuator, wherein actuation of the first actuator in a first direction tensions the first pull wire forming a proximal curve in a first arcuate direction along the intermediate portion of the elongate shaft in a first plane, and wherein actuation of the first actuator in a second direction opposite the first direction releases the tension in the first pull wire allowing the proximal curve to return to an unbiased configuration, wherein actuation of the second actuator in a first direction tensions the second pull wire forming a distal curve in a first curved direction along the distal portion of the elongate shaft in a second plane, and wherein actuation of the second actuator in a second direction opposite the first direction of the second actuator releases the tension in the second pull wire allowing the distal curve to return to an unbiased configuration.

Example 2 is the sheath of Example 1, wherein the second plane is transverse to the first plane.

Example 3 is the sheath of any of Examples 1-2, further comprising a pusher rod coupled to the first actuator and wherein actuation of the first actuator in the first direction engages the pusher rod with the second actuator and moves the second actuator in cooperation with the first actuator thereby preventing slack in the second pull wire.

Example 4 is the sheath of any of Examples 1-3, further comprising a third pull wire having a proximal end and a distal end, the third pull wire extending along the elongate shaft, wherein the distal end of the third pull wire is coupled to the intermediate portion of the elongate shaft at a position opposite the first pull wire and the proximal end of the third pull wire is coupled to the first actuator, and wherein actuation of the first actuator in the second direction opposite the first direction tensions the third pull wire so that the proximal curve curves in an opposite direction relative to the first arcuate direction along the intermediate portion of the elongate shaft and in the first plane.

Example 5 is the sheath of any of Examples 1-4, further comprising a fourth pull wire and a third actuator, the third actuator disposed on the handle, the fourth pull wire having a proximal end and a distal end and extending along the elongate shaft, wherein the distal end of the fourth pull wire is coupled to the distal portion of the elongate shaft at a position opposite the second pull wire and the proximal end of the fourth pull wire is coupled to the third actuator, and wherein actuation of the third actuator in a first direction tensions the fourth pull wire so that the distal curve curves in an opposite direction relative to the first curved direction along the distal portion of the elongate shaft and in the second plane, and wherein actuation of the third actuator in a second direction opposite the first direction of the third actuator releases the tension in the fourth pull wire allowing the distal curve to return to an unbiased configuration.

Example 6 is the sheath of any of Examples 1-5, further comprising a fifth pull wire and a fourth actuator, the fourth actuator disposed on the handle, the fifth pull wire having a proximal end and a distal end and extending along the elongate shaft, wherein the distal end of the fifth pull wire is coupled to the distal portion of the elongate shaft at a position circumferentially offset from the second and fourth pull wires and the proximal end of the fifth pull wire is coupled to the fourth actuator, and wherein actuation of the fourth actuator in a first direction tensions the fifth pull wire so that the distal curve curves in a second curved direction along the distal portion of the elongate shaft and in the first plane, and wherein actuation of the fourth actuator in a second direction opposite the first direction of the fourth actuator releases the tension in the fifth pull wire allowing the distal curve to return to an unbiased configuration.

Example 7 is the sheath of any of Examples 1-6, further comprising a sixth pull wire and a fifth actuator, the fifth actuator disposed on the handle, the sixth pull wire having a proximal end and a distal end and extending along the elongate shaft, wherein the distal end of the sixth pull wire is coupled to the distal portion of the elongate shaft at a position opposite the fifth pull wire and the proximal end of the sixth pull wire is coupled to the fifth actuator, and wherein actuation of the fifth actuator in a first direction tensions the sixth pull wire so that the distal curve curves in an opposite direction relative to the second curved direction along the distal portion of the elongate shaft and in the first plane, and wherein actuation of the fifth actuator in a second direction opposite the first direction of the fifth actuator releases the tension in the sixth pull wire allowing the distal curve to return to an unbiased configuration.

Example 8 is the sheath of any of Examples 1-7, wherein the second actuator, the third actuator, the fourth actuator, or the fifth actuator comprises a slider.

Example 9 is the sheath of any of Examples 1-9, wherein the second actuator, the third actuator, the fourth actuator, or the fifth actuator comprises a lock for preventing slidable movement thereof.

Example 10 is the sheath of any of Examples 1-9, wherein the proximal curve has a radius of curvature, and the distal curve has a radius of curvature smaller than the radius of curvature of the proximal curve, or the proximal curve may have a radius of curvature smaller than the distal curve.

Example 11 is the sheath of any of Examples 1-10, wherein the first actuator comprises a rotatable wheel threadably engaged with a threaded shuttle, wherein rotation of the rotatable wheel is translated into linear motion of the shuttle.

Example 12 is the sheath of any of Examples 1-11, further comprising indicia on the first actuator or the second actuator configured to identify actuation of the actuator element with a change in the shape of the proximal or distal curves.

Example 13 is the sheath of any of Examples 1-12, further comprising a dilator disposed in the lumen of the elongate shaft, wherein the dilator comprises a proximal end, a distal end, and a middle portion disposed therebetween, wherein the middle portion is more flexible than the proximal or distal ends of the dilator thereby facilitating steering of the elongate shaft.

Example 14 is the sheath of any of Examples 1-13, wherein the distal curve comprises a first distal curve that curves the elongate shaft in the second plane and a second distal curve that curves the elongate shaft in a third plane transverse to the first plane, thereby forming an infinitely navigable sheath.

Example 15 is a method of steering a sheath, said method comprising: providing an elongate shaft having a proximal portion, a distal portion, an intermediate portion disposed between the proximal and distal portions, and a lumen extending between the proximal and distal portions; actuating a first actuator in a first direction, the first actuator disposed on a handle coupled to the proximal portion of the elongate shaft thereby tensioning a first pull wire coupled to the intermediate portion; forming a proximal curve in the intermediate portion in a first plane; actuating a second actuator in a first direction, the second actuator disposed on the handle thereby tensioning a second pull wire coupled to the distal portion; and forming a distal curve in the distal portion in a second plane.

Example 16 is the method of Example 15, wherein actuating the first actuator comprises rotating a rotatable wheel.

Example 17 is the method of any of Examples 15-16, wherein actuating the second actuator comprises sliding a slider.

Example 18 is the method of any of Examples 15-17, wherein the first plane is transverse to the second plane.

Example 19 is the method of any of Examples 15-18, wherein the distal curve has a radius of curvature and the proximal curve has a radius of curvature larger than the radius of curvature of the distal curve.

Example 20 is the method of any of Examples 15-19, further comprising actuating the first actuator in a second direction opposite the first direction thereby releasing tension on the first pull wire and tensioning a third pull wire coupled to the intermediate portion, and reforming the proximal curve in the intermediate portion in an opposite direction and in the first plane.

Example 21 is the method of any of Examples 15-20, further comprising actuating a third actuator in a first direction, the third actuator disposed on the handle thereby tensioning a fourth pull wire coupled to the distal portion and reforming the distal curve in the distal portion in an opposite direction and in the second plane.

Example 22 is the method of any of Examples 15-21, further comprising actuating a fourth actuator in a first direction, the fourth actuator disposed on the handle thereby tensioning a fifth pull wire coupled to the distal portion and reforming the distal curve in the distal portion in the first plane.

Example 23 is the method of any of Examples 15-22, further comprising actuating a fifth actuator in a first direction, the fifth actuator disposed on the handle thereby tensioning a sixth pull wire coupled to the distal portion and reforming the distal curve in the distal portion in an opposite direction and in the rst plane.

Example 24 is the method of any of Examples 15-23, further comprising locking the second actuator in position with a lock.

Example 25 is the method of any of Examples 15-24, further comprising slidably inserting a dilator into the lumen, wherein the dilator comprises a proximal end, a distal end, and a middle portion disposed therebetween, wherein the middle portion is more flexible than the proximal or distal ends.

Example 26 is the method of any of Examples 15-25, wherein actuating the first actuator comprises moving a rod coupled to the first actuator and engaging the rod with the second actuator thereby moving the second actuator cooperatively with first actuator and preventing slack in the second pull wire.

Example 27 is the method of any of Examples 15-26, further comprising actuating the first actuator in a second direction opposite the first direction thereby relieving the tension in the first pull wire and returning the proximal curve to an unbiased position.

Example 28 is the method of any of Examples 15-27, further comprising actuating the second actuator in a second direction opposite the first direction thereby relieving the tension in the second pull wire and returning the distal curve to an unbiased position.

Example 29 is the method of any of Examples 15-28, further comprising forming a second distal curve simultaneously with the distal curve, the second distal curve disposed in a third plane transverse to the second plane, thereby allowing infinite navigation of the elongate shaft.

In Example 30, the apparatuses or methods of any one or any combination of Examples 1-29 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third." etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A steerable sheath comprising:
   an elongate shaft comprising a proximal portion, a distal portion, an intermediate portion disposed between the proximal portion and the distal portion, and a lumen extending between the proximal and distal portions;
   a first pull wire having a proximal end and a distal end, the first pull wire extending along the elongate shaft;
   a second pull wire having a proximal end and a distal end, the second pull wire extending along the elongate shaft;
   a handle coupled with the proximal portion of the elongate shaft;
   a first actuator disposed on the handle; and
   a second actuator disposed on the handle,
   wherein the distal end of the first pull wire is coupled to the intermediate portion of the elongate shaft and the proximal end of the first pull wire is coupled to the first actuator,
   wherein the distal end of the second pull wire is coupled to the distal portion of the elongate shaft and the proximal end of the second pull wire is coupled to the second actuator,
   wherein actuation of the first actuator in a first direction tensions the first pull wire forming a proximal curve in a first arcuate direction along the intermediate portion of the elongate shaft in a first plane, and wherein actuation of the first actuator in a second direction opposite the first direction releases the tension in the first pull wire allowing the proximal curve to return to an unbiased configuration,
   wherein actuation of the second actuator in a first direction tensions the second pull wire forming a distal curve in a first curved direction along the distal portion of the elongate shaft in a second plane, and wherein actuation of the second actuator in a second direction opposite the first direction of the second actuator releases the tension in the second pull wire allowing the distal curve to return to an unbiased configuration.

2. The sheath of claim 1, wherein the second plane is transverse to the first plane.

3. The sheath of claim 1, further comprising a pusher rod coupled to the first actuator and wherein actuation of the first actuator in the first direction engages the pusher rod with the second actuator and moves the second actuator in cooperation with the first actuator thereby preventing slack in the second pull wire.

4. The sheath of claim 1, further comprising a third pull wire having a proximal end and a distal end, the third pull wire extending along the elongate shaft,
   wherein the distal end of the third pull wire is coupled to the intermediate portion of the elongate shaft at a position opposite the first pull wire and the proximal end of the third pull wire is coupled to the first actuator, and
   wherein actuation of the first actuator in the second direction opposite the first direction tensions the third pull wire so that the proximal curve curves in an opposite direction relative to the first arcuate direction along the intermediate portion of the elongate shaft and in the first plane.

5. The sheath of claim 1, further comprising a fourth pull wire and a third actuator, the third actuator disposed on the handle, the fourth pull wire having a proximal end and a distal end and extending along the elongate shaft,
   wherein the distal end of the fourth pull wire is coupled to the distal portion of the elongate shaft at a position opposite the second pull wire and the proximal end of the fourth pull wire is coupled to the third actuator, and
   wherein actuation of the third actuator in a first direction tensions the fourth pull wire so that the distal curve curves in an opposite direction relative to the first curved direction along the distal portion of the elongate shaft and in the second plane, and wherein actuation of the third actuator in a second direction opposite the first direction of the third actuator releases the tension in the fourth pull wire allowing the distal curve to return to an unbiased configuration.

6. The sheath of claim 5, further comprising a fifth pull wire and a fourth actuator, the fourth actuator disposed on the handle, the fifth pull wire having a proximal end and a distal end and extending along the elongate shaft, wherein the distal end of the fifth pull wire is coupled to the distal portion of the elongate shaft at a position circumferentially offset from the second and fourth pull wires and the proximal end of the fifth pull wire is coupled to the fourth actuator, and wherein actuation of the fourth actuator in a first direction tensions the fifth pull wire so that the distal curve curves in a second curved direction along the distal portion of the elongate shaft and in the first plane, and wherein actuation of the fourth actuator in a second direction opposite the first direction of the fourth actuator releases the tension in the fifth pull wire allowing the distal curve to return to an unbiased configuration.

7. The sheath of claim 6, further comprising a sixth pull wire and a fifth actuator, the fifth actuator disposed on the handle, the sixth pull wire having a proximal end and a distal end and extending along the elongate shaft, wherein the distal end of the sixth pull wire is coupled to the distal portion of the elongate shaft at a position opposite the fifth pull wire and the proximal end of the sixth pull wire is coupled to the fifth actuator, and wherein actuation of the fifth actuator in a first direction tensions the sixth pull wire so that the distal curve curves in an opposite direction relative to the second curved direction along the distal portion of the elongate shaft and in the first plane, and wherein actuation of the fifth actuator in a second direction opposite the first direction of the fifth actuator releases the tension in the sixth pull wire allowing the distal curve to return to an unbiased configuration.

8. The sheath of claim 7, wherein the second actuator, the third actuator, the fourth actuator, or the fifth actuator comprises a slider.

9. The sheath of claim 8, wherein the second actuator, the third actuator, the fourth actuator, or the fifth actuator comprises a lock for preventing slidable movement thereof.

10. The sheath of claim 1, wherein the proximal curve has a radius of curvature, and the distal curve has a radius of curvature smaller than the radius of curvature of the proximal curve, or the proximal curve has a radius of curvature smaller than the radius of curvature of the distal curve.

11. The sheath of claim 1, wherein the first actuator comprises a rotatable wheel threadably engaged with a threaded shuttle, wherein rotation of the rotatable wheel is translated into linear motion of the shuttle.

12. The sheath of claim 1, further comprising indicia or an indicator on the first actuator or the second actuator configured to identify actuation of the actuator element with a change in the shape of the proximal or distal curves.

13. The sheath of claim 1, further comprising a dilator disposed in the lumen of the elongate shaft, wherein the dilator comprises a proximal end, a distal end, and a middle portion disposed therebetween, wherein the middle portion is more flexible than the proximal or distal ends of the dilator thereby facilitating steering of the elongate shaft.

14. The sheath of claim 1, wherein the distal curve comprises a first distal curve that curves the elongate shaft in the second plane and a second distal curve that curves the elongate shaft in a third plane transverse to the first plane, thereby forming an infinitely navigable sheath.

15. A method of steering a sheath, said method comprising:

providing an elongate shaft having a proximal portion, a distal portion, an intermediate portion disposed between the proximal and distal portions, and a lumen extending between the proximal and distal portions;

actuating a first actuator in a first direction, the first actuator disposed on a handle coupled to the proximal portion of the elongate shaft thereby tensioning a first pull wire coupled to the intermediate portion;

forming a proximal curve in the intermediate portion in a first plane;

actuating a second actuator in a first direction, the second actuator disposed on the handle thereby tensioning a second pull wire coupled to the distal portion; and forming a distal curve in the distal portion in a second plane.

16. The method of claim 15, wherein actuating the first actuator comprises rotating a rotatable wheel.

17. The method of claim 15, wherein actuating the second actuator comprises sliding a slider.

18. The method of claim 15, wherein the first plane is transverse to the second plane.

19. The method of claim 15, wherein the distal curve has a radius of curvature and the proximal curve has a radius of curvature larger than the radius of curvature of the distal curve.

20. The method of claim 15, further comprising actuating the first actuator in a second direction opposite the first direction thereby releasing tension on the first pull wire and tensioning a third pull wire coupled to the intermediate portion, and reforming the proximal curve in the intermediate portion in an opposite direction and in the first plane.

21. The method of claim 15, further comprising actuating a third actuator in a first direction, the third actuator disposed on the handle thereby tensioning a fourth pull wire coupled to the distal portion and reforming the distal curve in the distal portion in an opposite direction and in the second plane.

22. The method of claim 21, further comprising actuating a fourth actuator in a first direction, the fourth actuator disposed on the handle thereby tensioning a fifth pull wire coupled to the distal portion and reforming the distal curve in the distal portion in the first plane.

23. The method of claim 22, further comprising actuating a fifth actuator in a first direction, the fifth actuator disposed on the handle thereby tensioning a sixth pull wire coupled to the distal portion and reforming the distal curve in the distal portion in an opposite direction and in the first plane.

24. The method of claim 15, further comprising locking the second actuator in position with a lock.

25. The method of claim 15, further comprising slidably inserting a dilator into the lumen, wherein the dilator comprises a proximal end, a distal end, and a middle portion disposed therebetween, wherein the middle portion is more flexible than the proximal or distal ends.

26. The method of claim 15, wherein actuating the first actuator comprises moving a rod coupled to the first actuator and engaging the rod with the second actuator thereby moving the second actuator cooperatively with first actuator and preventing slack in the second pull wire.

27. The method of claim 15, further comprising actuating the first actuator in a second direction opposite the first direction thereby relieving the tension in the first pull wire and returning the proximal curve to an unbiased position.

28. The method of claim 15, further comprising actuating the second actuator in a second direction opposite the first direction thereby relieving the tension in the second pull wire and returning the distal curve to an unbiased position.

29. The method of claim 15, further comprising forming a second distal curve simultaneously with the distal curve, the second distal curve disposed in a third plane transverse to the second plane, thereby allowing infinite navigation of the elongate shaft.

\* \* \* \* \*

UNITED STATES PATENT AND TRADEMARK OFFICE
CERTIFICATE OF CORRECTION

PATENT NO. : 11,344,702 B2
APPLICATION NO. : 16/944997
DATED : May 31, 2022
INVENTOR(S) : Subramaniam et al.

It is certified that error appears in the above-identified patent and that said Letters Patent is hereby corrected as shown below:

In the Specification

In Column 3, Line 6, delete "maybe" and insert --may be-- therefor

In Column 3, Line 61, delete "maybe" and insert --may be-- therefor

In Column 4, Line 4, delete "200" and insert --202-- therefor

In Column 5, Line 16, delete "maybe" and insert --may be-- therefor

In Column 5, Line 38, delete "300" and insert --310-- therefor

In Column 5, Line 44, delete "304, 306.308" and insert --304, 306, 308-- therefor In Column 6, Line 18, delete "valve." and insert --valve,-- therefor In Column 6, Line 36, delete "frst" and insert --first-- therefor In Column 8, Line 67, delete "maybe" and insert --may be-- therefor In Column 10, Line 10, delete "maybe" and insert --may be-- therefor In Column 10, Line 42, delete "maybe" and insert --may be-- therefor In Column 11, Line 39, delete "120" and insert --1220-- therefor In Column 11, Line 43, delete "11218," and insert --1218,-- therefor In Column 13, Line 12, delete "maybe" and insert --may be-- therefor Signed and Sealed this
Twenty-second Day of November, 2022

Katherine Kelly Vidal
*Director of the United States Patent and Trademark Office*

In Column 13, Line 38, delete "maybe" and insert --may be-- therefor

In Column 13, Line 44, delete "maybe be" and insert --may be-- therefor

In Column 13, Line 45, delete "shat" and insert --shaft-- therefor

In Column 16, Line 37, delete "rst" and insert --first-- therefor

In Column 17, Line 28, delete "B."" and insert --B,"-- therefor

In Column 17, Line 38, delete ""third."" and insert --"third,"-- therefor